US007288562B2

(12) United States Patent
Mehta et al.

(10) Patent No.: US 7,288,562 B2
(45) Date of Patent: Oct. 30, 2007

(54) FLUORO AND SULPHONYLAMINO CONTAINING 3,6-DISUBSTITUTED AZABICYCLO (3.1.0) HEXANE DERIVATIVES AS MUSCARINIC RECEPTOR ANTAGONISTS

(75) Inventors: Anita Mehta, Plainfield, IL (US); Jang Bahadur Gupta, Dusseldorf (DE)

(73) Assignee: Ranbaxy Laboratories Limited, Gurgaon (IN)

( * ) Notice: Subject to any disclaimer, the term of this patent is extended or adjusted under 35 U.S.C. 154(b) by 66 days.

(21) Appl. No.: 10/525,439

(22) PCT Filed: Aug. 23, 2002

(86) PCT No.: PCT/IB02/03433

§ 371 (c)(1),
(2), (4) Date: Aug. 1, 2005

(87) PCT Pub. No.: WO2004/018422

PCT Pub. Date: Mar. 4, 2004

(65) Prior Publication Data

US 2006/0004083 A1  Jan. 5, 2006

(51) Int. Cl.
*A61K 31/403* (2006.01)
*C07D 209/52* (2006.01)
(52) U.S. Cl. ........................... 514/412; 548/515
(58) Field of Classification Search ............... 548/515; 514/412
See application file for complete search history.

(56) References Cited

U.S. PATENT DOCUMENTS

| | | | | |
|---|---|---|---|---|
| 3,176,019 | A | 3/1965 | Campbell et al. | 260/293.4 |
| 5,281,601 | A | 1/1994 | Cross et al. | 514/320 |
| 5,397,800 | A | 3/1995 | Alker et al. | 514/413 |
| 5,735,690 | A | 4/1998 | Malentacca | 433/102 |
| 5,948,792 | A | 9/1999 | Tsuchiya et al. | 514/317 |
| 6,130,232 | A | 10/2000 | Mase et al. | 514/318 |
| 6,174,900 | B1 | 1/2001 | Okada et al. | 514/317 |
| 7,049,444 | B2* | 5/2006 | Banks et al. | 548/452 |

FOREIGN PATENT DOCUMENTS

| | | |
|---|---|---|
| EP | 0 325 571 | 7/1989 |
| EP | 0 388 054 | 9/1990 |
| EP | 0 413 455 | 2/1991 |
| EP | 0 801 067 | 10/1997 |
| GB | 940540 | 10/1963 |
| JP | 92921/1994 | 4/1994 |
| JP | 135989/1994 | 5/1995 |
| WO | WO91/09013 | 6/1991 |
| WO | WO93/16018 | 8/1993 |
| WO | WO93/16048 | 8/1993 |
| WO | WO95/15312 | 6/1995 |
| WO | WO95/15327 | 6/1995 |
| WO | WO96/33973 | 10/1996 |
| WO | WO97/36906 | 10/1997 |
| WO | WO97/45414 | 12/1997 |
| WO | WO98/05641 | 2/1998 |
| WO | WO98/29402 | 7/1998 |

OTHER PUBLICATIONS

Morissette et al. Advanced Drug Delivery Reviews 2004, 56, 275-300.*
Kubo et al., "Cloning, sequencing and expression of complementary DNA encoding the muscarinic acetylcholine receptor", *Nature*, 323(2):411-416 (1986).
Bonner et al., "Identification of a Family of Muscarinic Acetylcholine Receptor Genes", *Science*, 237:527-531 (1987).
Eglen et al., "Muscarinic receptor ligands and their therapeutic potential", *Current Opinion in Chemical Biology*, 3:426-432 (1999).
Eglen et al., "Therapeutic opportunities from muscarinic receptor research", *Trends in Pharmacological Sciences*, 22(8):409-414 (2001).
Felder et al., "Therapeutic Opportunities for Muscarinic Receptors in the Central Nervous System", *Journal of Medicinal Chemistry*, 43(23):4333-4353 (2000).
Broadley and Kelly, "Muscarinic Receptor Agonists and Antagonists", *Molecules*, 6:142-193 (2001).
Birdsall et al., "Muscarinic receptors: it's a knockout", *Trends in Pharmacological Sciences*, 22(5):215-219 (2001).
de Groat and Yoshimura, "Pharmacology of the Lower Urinary Tract", *Annual Review of Pharmacology and Toxicology*, 41:691-721 (2001).
Steers, "The future direction of neuro-urology drug research", *Current Opinion in CPNS Investigational Drugs*, 2(3):268-282.
Chapple, "Muscarinic receptor antagonists in the treatment of overactive bladder", *Urology*, 55(Suppl. 5A):33-46 (2000).
Steers, Barrot, Wein, "Voiding dysfunction: diagnosis classification and management", In: *Adult and Pediatric Urology*, ed. Gillenwater, Grayhack, Howards, Duckett. Mosby, St. Louis, MO; 1220-1325, 3rd edition (1996).
Sagara et al, "Cyclohexylmethylpiperidinyltriphenylpropioamide: A Selective Muscarinic $M_3$ Antagonist Discriminating against the Other Receptor Subtypes", *Journal of Medicinal Chemistry*, 45(4):984-987 (2002).

(Continued)

*Primary Examiner*—Rebecca Anderson
*Assistant Examiner*—Jason M Nolan
(74) *Attorney, Agent, or Firm*—George E. Heibel, Esq.; Jayadeip R. Deshmukh, Esq.

(57) ABSTRACT

This invention generally relates to the derivatives of novel 3,6 disubstituted azabicyclo[3.1.0] hexane's. The compounds of this invention are MUSCARINIC receptor antagonists which are useful, inter-ail for the treatment of various diseases of the respiratory, urinary and gastrointestinal systems mediated through MUSCARINIC receptors. The invention also relates to processes for the preparation of the compounds of the invention, pharmaceutical compositions containing the compounds of the present invention and the methods of treating the diseases mediated through MUSCARINIC receptors.

27 Claims, No Drawings

OTHER PUBLICATIONS

Mase et al., "Synthesis of a Muscarinic Receptor Antagonist via a Diastereoselective Michael Reaction, Selective Deoxyfluorination and Aromatic Metal-Halogen Exchange Reaction", *Journal of Organic Chemistry*, 66(20):6775-6786 (2001).

Mitsuya et al., "Discovery of a Muscarinic $M_3$ Receptor Antagonist with High Selectivity for $M_3$ Over $M_2$ Receptors Among 2-[(1S,3S)-3-Sulfonylaminocyclopentyl]phenylacetamide Derivatives" *Bioorganic & Medicinal Chemistry*, 8:825-832 (2000).

Grover et al., "Chiral Mandelic Acid Template Provides a Highly Practical Solution for (S)-Oxybutynin Synthesis", *Journal of Organic Chemistry*, 65:6283-6287 (2000).

Moriya et al., "Affinity Profiles of Various Muscarinic Antagonists for Cloned Human Muscarinic Acetylcholine Receptor (mAChR) Subtypes and mAChRs in Rat Heart and Submandibular Gland", *Life Sciences*, 64(25):2351-2358 (1999).

Cheng and Prusoff, "Relationship between the inhibition constant ($KI$) and the concentration of inhibitor which causes 50 per cent inhibition ($I50$) of an enzymatic reaction", *Biochemical Pharmacology*, 22:3099-3108 (1973).

Jeppesen et al., "1-(1,2,5-Thiadiazol-4-yl)-4-azatricyclo[2.2.1.$0^{2,6}$]heptanes as New Potent Muscarinic $M_1$ Agonists: Structure-Activity Relationship for 3-Aryl-2-propyn-1-yloxy and 3-Aryl-2-propyn-1-ylthio Derivatives", *Journal of Medicinal Chemistry*, 42(11):1999-2006 (1999).

\* cited by examiner

FLUORO AND SULPHONYLAMINO CONTAINING 3,6-DISUBSTITUTED AZABICYCLO (3.1.0) HEXANE DERIVATIVES AS MUSCARINIC RECEPTOR ANTAGONISTS

FIELD OF THE INVENTION

This invention generally relates to the derivatives of novel 3,6 disubstituted azabicyclo[3.1.0]hexanes.

The compounds of this invention are muscarinic receptor antagonists which are useful, inter-alia for the treatment of various diseases of the respiratory, urinary and gastrointestinal systems mediated through muscarinic receptors.

The invention also relates to processes for the preparation of the compounds of the invention, pharmaceutical compositions containing the compounds of the present invention and the methods of treating the diseases mediated through muscarinic receptors.

BACKGROUND OF THE INVENTION

Muscarinic receptors as members of the G Protein Coupled Receptors (GPCRs) are composed of a family of 5 receptor sub-types ($M_1$, $M_2$, $M_3$, $M_4$ and $M_5$) and are activated by the neurotransmitter acetylcholine. These receptors are widely distributed on multiple organs and tissues and are critical to the maintenance of central and peripheral cholinergic neurotransmission. The regional distribution of these receptor sub-types in the brain and other organs has been documented. For example, the $M_1$ subtype is located primarily in neuronal tissues such as cereberal cortex and autonomic ganglia, the $M_2$ subtype is present mainly in the heart where it mediates cholinergically induced bradycardia, and the $M_3$ subtype is located predominantly on smooth muscle and salivary glands (*Nature*, 1986; 323: 411; Science, 1987; 237: 527).

A review in Current opinions in Chemical Biology, 1999; 3: 426, as well as in Trends in Pharmacological Sciences, 2001; 22: 409 by Eglen et. al., describe the biological potentials of modulating muscarinic receptor subtypes by ligands in different disease conditions like Alzheimer's disease, pain, urinary disease condition, chronic obstructive pulmonary disease etc.

A review in J. Med. Chem., 2000; 43: 4333 by Christian C. Felder et. al. describes therapeutic opportunities for muscarinic receptors in the central nervous system and elaborates on muscarinic receptor structure and function, pharmacology and their therapeutic uses.

The pharmacological and medical aspects of the muscarinic class of acetylcholine agonists and antagonists are presented in a review in Molecules, 2001, 6: 142.

N. J. M. Birdsall et. al. in Trends in Pharmacological Sciences, 2001; 22: 215 have also summarized the recent developments on the role of different muscarinic receptor subtypes using different muscaranic receptor of knock out mice.

Muscarinic agonists such as muscarine and pilocarpine and antagonists is such as atropine have been known for over a century, but little progress has been made in the discovery of receptor subtype-selective compounds making it difficult to assign specific functions to the individual receptors. Although classical muscarinic antagonists such as atropine are potent bronchodilators, their clinical utility is limited due to high incidence of both peripheral and central adverse effects such as tachycardia, blurred vision, dryness of mouth, constipation, dementia, etc. Subsequent development of the quarterly derivatives of atropine such as ipratropium bromide are better tolerated than parenterally administered options but most of them are not ideal anti-cholinergic bronchodilators due to lack of selectivity for muscarinic receptor sub-types. The existing compounds offer limited therapeutic benefit due to their lack of selectivity resulting in dose limiting side-effects such as thirst, nausea, mydriasis and those associated with the heart such as tachycardia mediated by the $M_2$ receptor.

Annual review of Pharmacological Toxicol., 2001; 41: 691, describes the pharmacology of the lower urinary tract infections. Although anti muscarinic agents such as oxybutynin and tolterodine that act non-selectively on muscarinic receptors have been used for many years to treat bladder hyperactivity, the clinical effectiveness of these agents has been limited due to the side effects such as dry mouth, blurred vision and constipation. Tolterodine is considered to be generally better tolerated than oxybutynin. (W. D. Steers et. al. in Curr. Opin. Invest. Drugs, 2: 268, C. R. Chapple et. al. in Urology, 55: 33), Steers WD, Barrot DM, Wein AJ, 1996, Voiding dysfunction: diagnosis classification and management. In Adult and Pediatric Urology, ed. JY Gillenwatter, JT Grayhack, SS Howards, JW Duckett, pp 1220-1325, St. Louis, Mo.; Mosby. $3^{rd}$ edition.)

Despite these advances, there remains a need for development of new highly selective muscarinic antagonists which can interact with distinct subtypes, thus avoiding the occurrence of adverse effects.

Compounds having antagonistic activity against muscarinic receptors have been described in Japanese patent application Laid Open Number 92921/1994 and 135958/1994; WO 93/16048; U.S. Pat. No. 3,176,019; GB 940,540; EP 0325 571; WO 98/29402; EP 0801067; EP 0388054; WO 9109013; U.S. Pat. No. 5,281,601. U.S. Pat. Nos. 6,174,900, 6,130,232 and 5,948,792; WO 97/45414 are related to 1,4-disubstituted piperidine derivatives; WO 98/05641 describes fluorinated, 1,4-disubstitued piperidine derivatives; WO 93/16018 and WO96/33973 are other close art references.

A report in J. Med. Chem., 2002; 44:984, describes cyclohexylmethyl piperidinyl triphenylpropioamide derivatives as selective $M_3$ antagonist discriminating against the other receptor subtypes.

SUMMARY OF THE INVENTION

The present invention provides novel fluoro and sulphonylamino containing 3,6-disubstituted azabicyclo[3.1.0] hexanes as muscarinic receptor antagonists which are useful as safe and effective therapeutic or prophylactic agents for the treatment of various diseases of the respiratory, urinary and gastrointestinal systems and process for the synthesis of the novel compounds. Substitution on the cycloalkyl moeity improves both metabolic stability as well as subtype selectivity.

The invention also provides pharmaceutical compositions containing the novel compounds together with acceptable carriers, excipients or diluents which are useful for the treatment of various diseases of the respiratory, urinary and gastrointestinal systems.

The present invention also includes within its scope prodrugs of the novel compounds. In general, such prodrugs will be functionalized derivatives of these compounds which readily get converted in vivo into the defined compounds. Conventional procedures for the selection and preparation of suitable prodrugs are known to the artisan skilled in the art.

The invention also includes the enantiomers, diastereomers, N-oxides, polymorphs, pharmaceutically acceptable salts and pharmaceutically acceptable solvates of these compounds as well as metabolites having the same type of activity.

The invention further includes pharmaceutical compositions comprising the compounds of the present invention, their prodrugs, metabolites, enantiomers, diastereomers, N-oxides, polymorphs, solvates or pharmaceutically acceptable salts thereof, in combination with a pharmaceutically acceptable carrier and optionally included excipients.

Other advantages of the invention will be set forth in the description which follows, and in part will be apparent from the description or may be learnt by the practice of the invention. The objects and the advantages of the invention may be realized and obtained by means of the mechanisms and combinations pointed out in the appended claims.

In accordance with one aspect of the present invention, there is provided a compound having the structure of Formula I:

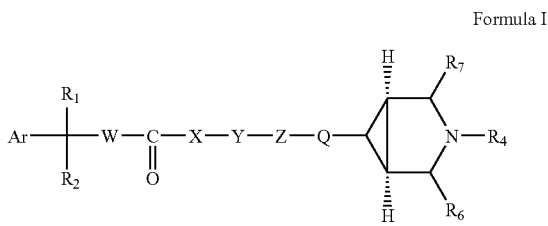

Formula I and its pharmaceutically acceptable salts, pharmaceutically acceptable solvates, esters, enantiomers, diastereomers, N-oxides, polymorphs, prodrugs, metabolites, wherein Ar represents an aryl or a heteroaryl ring having 1-2 hetero atoms selected from the group consisting of oxygen, sulphur and nitrogen atoms, the aryl or heteroaryl rings may be unsubstituted or substituted by one to three substituents independently selected from lower alkyl ($C_1$-$C_4$), lower perhalo alkyl ($C_1$-$C_4$), cyano, hydroxy, nitro, lower alkoxy ($C_1$-$C_4$), lower perhalo alkoxy ($C_1$-$C_4$), unsubstituted amino, N-lower alkyl ($C_1$-$C_4$) amino or N-lower alkyl ($C_1$-$C_4$) amino carbonyl;

$R_1$ represents a hydrogen, hydroxy, hydroxymethyl, amino, alkoxy, carbamoyl or halogen (e.g. fluorine, chlorine, bromine and iodine);

$R_2$ represents $C_3$-$C_7$ cycloalkyl ring in which from 1 to 4 hydrogen atoms are substituted with fluorine atoms, or sulphonamide derivatives;

W represents $(CH_2)_p$, where p represents 0 to 1;

X represents an oxygen, sulphur, nitrogen or no atom;

Y represents $CHR_5CO$ wherein $R_5$ represents hydrogen or methyl or $(CH_2)_q$ wherein q represents 0 to 4;

Z represents oxygen, sulphur or $NR_{10}$, wherein $R_{10}$ represents hydrogen, $C_{1-6}$ alkyl;

Q represents $(CH_2)_n$ wherein n represents 1 to 4, or $CHR_8$ wherein $R_8$ represents H. OH, $C_{1-6}$, alkyl, alkenyl, alkoxy or $CH_2CHR_9$, wherein $R_9$ represents H, OH, lower alkyl ($C_1$-$C_4$) or lower alkoxy ($C_1$-$C_4$);

$R_6$ and $R_7$ are independently selected from H, $CH_3$, COOH, $CONH_2$, $NH_2$, $CH_2NH_2$; and $R_4$ represents a $C_1$-$C_{15}$ saturated or unsaturated aliphatic hydrocarbon group in which from 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on the ring in said arylalkyl, arylalkenyl, hetero arylalkenyl group may be substituted with lower alkyl ($C_1$-$C_4$), lower perhalo alkyl ($C_1$-$C_4$), cyano, hydroxyl, nitro, lower alkoxycarbonyl, halogen, lower alkoxy ($C_1$-$C_4$), lower perhaloalkoxy ($C_1$-$C_4$), unsubstituted amino, N-lower alkylamino ($C_1$-$C_4$), N-lower alkylamino carbonyl ($C_1$-$C_4$).

In accordance with a second aspect of the present invention, there is provided a compound having the structure of Formula II (Formula I, when $R_6$ and $R_7$=H) and its pharmaceutically acceptable salts, pharmaceutically acceptable solvates, esters, enantiomers, diastereomers, N-oxides, polymorphs, prodrugs, metabolites, wherein Ar, $R_1$, $R_2$, W, X, Y, Z, Q, and $R_4$ are as defined for Formula I.

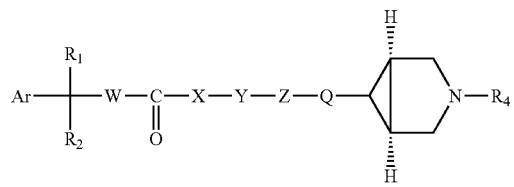

Formula II

In accordance with a third aspect of the present invention there is provided a compound having the structure of Formula III (Formula I wherein W is $(CH_2)_p$ where p=0, X is no atom and Y is $(CH_2)_q$ where q=0, $R_6$=H, $R_7$=H) and its pharmaceutically acceptable salts, pharmaceutically acceptable solvates, esters, enantiomers, diastereomers, N-oxides, polymorphs, prodrugs, metabolites, wherein Ar, $R_1$, $R_2$, Z, Q and $R_4$ are as defined for Formula I.

Formula III

In accordance with a fourth aspect of the present invention, there is provided a compound having the structure of Formula IV [Formula I when W is $(CH_2)_p$ where p=0, X is no atom and Y is $(CH_2)_q$ where q=0, $R_6$=H, $R_7$=H, $R_2$=

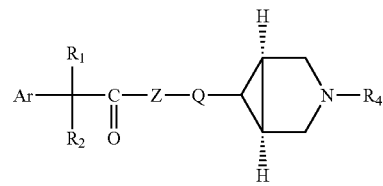

where $R_{11}$ is hydrogen or fluoro, $R_{12}$ is fluoro or sulphonamide derivatives and s represents 1 to 2, $R_1$ is hydroxy, Ar is phenyl], and its pharmaceutically acceptable solvates, esters, enantiomers, diastereomers, N-oxides, polymorphs, prodrugs, metabolites, wherein $R_4$, Z and Q are the same as defined for Formula I.

Formula IV

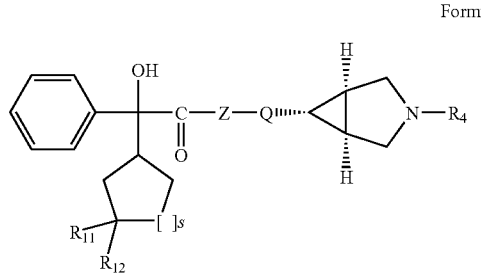

In accordance with a fifth aspect of the present invention, there is provided a method for treatment or prophylaxis of an animal or human suffering from a disease or disorder of the respiratory, urinary and gastrointestinal systems, wherein the disease or disorder is mediated through muscarinic receptors.

In accordance with a sixth aspect of the present invention, there is provided a method for treatment or prophylaxis of an animal or human suffering from a disease or disorder associated with muscarinic receptors, comprising administering to a patient in need thereof, an effective amount of muscarinic receptor antagonist compound as described above.

In accordance with a seventh aspect of the present invention, there is provided a method for treatment or prophylaxis of an animal or human suffering from a disease or disorder of the urinary system which induce such urinary disorders as urinary incontinence, lower urinary tract symptoms (LUTS), etc.; respiratory system disorders such as bronchial asthma, chronic obstructive pulmonary disorders (COPD), pulmonary fibrosis, etc.; and gastrointestinal system disorders such as irritable bowel syndrome, obesity, diabetes and gastrointestinal hyperkinesis with compounds as described above, wherein the disease or disorder is associated with muscarinic receptors.

In accordance with the eighth aspect of the present invention, there are provided processes for preparing the compounds as described above.

The compounds of the present invention are novel and exhibit significant potency in terms of their activity, which was determined by in vitro receptor binding and functional assays and in vivo experiments using anaesthetized rabbit. The compounds that were found active in in vitro assay were tested in vivo. Some of the compounds of the present invention were found to be potent muscarinic receptor antagonists with high affinity towards $M_3$ receptors. Therefore, the present invention provides the pharmaceutical compositions for the possible treatment for the disease or disorders associated with muscarinic receptors. In addition, the compounds of the present invention can be administered orally or parenterally.

DETAILED DESCRIPTION OF THE INVENTION

The compounds of the present invention may be prepared by techniques well known in the art and familiar to the average synthetic organic chemist. In addition, the compounds of the present invention may be prepared by the following novel and inventive reaction sequences:

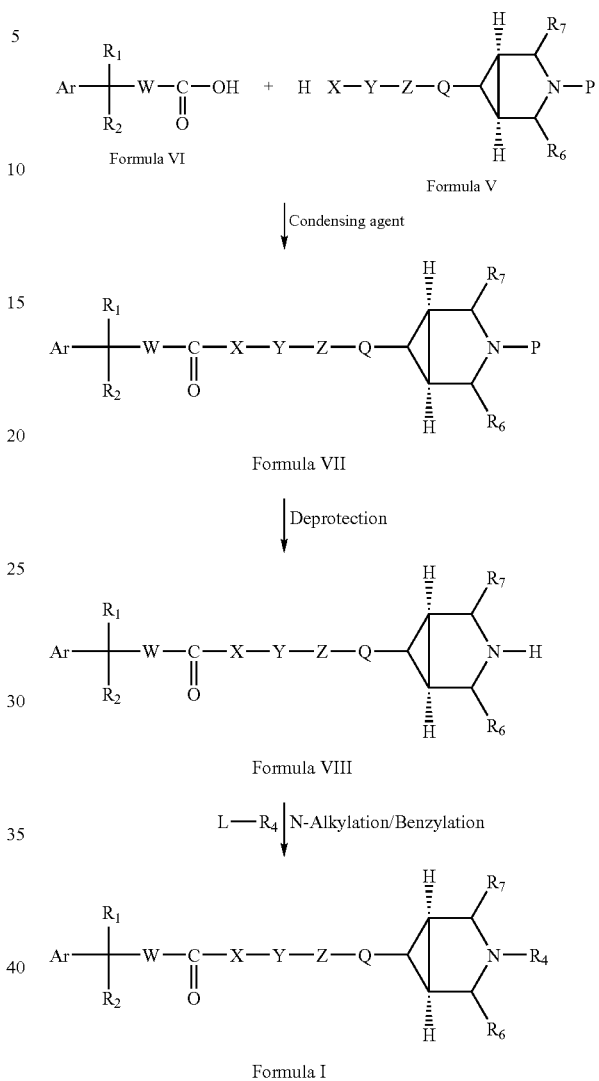

The compounds of Formula I of the present invention may be prepared by the reaction sequence as shown in Scheme I. The preparation comprises condensing a compound of Formula V with the compound of Formula VI wherein Ar represents an aryl or a heteroaryl ring having 1-2 hetero atoms selected from the group consisting of oxygen, sulphur and nitrogen atoms, the aryl or heteroaryl rings may be unsubstituted or substituted by one to three substituents independently selected from lower alkyl ($C_1$-$C_4$), lower perhalo alkyl ($C_1$-$C_4$), cyano, hydroxy, nitro, lower alkoxy ($C_1$-$C_4$), lower perhalo alkoxy ($C_1$-$C_4$), unsubstituted amino, N-lower alkyl ($C_1$-$C_4$) amino or N-lower alkyl ($C_1$-$C_4$) amino carbonyl;

$R_1$ represents a hydrogen, hydroxy, hydroxymethyl, amino, alkoxy, carbamoyl or halogen (e.g. fluorine, chlorine, bromine and iodine);

$R_2$ represents a $C_3$-$C_7$ cycloalkyl ring in which from 1 to 4 hydrogen atoms are substituted with fluorine atoms, or sulphonamide derivatives;

W represents $(CH_2)_p$, where p represents 0 to 1;

x represents an oxygen, sulphur, nitrogen or no atom;

Y represents CHR$_5$CO wherein R$_5$ represents hydrogen or methyl or (CH$_2$)$_q$ wherein q represents 0 to 4;

z represents oxygen, sulphur or NR$_{10}$, wherein R$_{10}$ represents hydrogen, C$_{1-6}$ alkyl;

Q represents (CH$_2$)$_n$ wherein n represents 1 to 4, or CHR$_8$ wherein R$_8$ represents H, OH, C$_{1-6}$, alkyl, alkenyl, alkoxy or CH$_2$CHR$_9$, wherein R$_9$ represents H, OH, lower alkyl (C$_1$-C$_4$) or lower alkoxy (C$_1$-C$_4$);

R$_6$ and R$_7$ are independently selected from H, CH$_3$, COOH, CONH$_2$, NH$_2$, CH$_2$NH$_2$; and P is any protecting group for an amino group, in the presence of a condensing agent to give a protected compound of Formula VII which on deprotection in the presence of a deprotecting agent in an organic solvent gives an unprotected intermediate of Formula VIII which is finally N-alkylated or benzylated with a suitable alkylating or benzylating agent, L-R$_4$ to give a compound of Formula I wherein L is any leaving group and R$_4$ represents C$_1$-C$_{15}$ saturated or unsaturated aliphatic hydrocarbon groups in which any 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on the ring in said arylalkyl, arylalkenyl, hetero arylalkenyl group may be substituted with lower alkyl (C$_1$-C$_4$), lower perhalo alkyl (C$_1$-C$_4$), cyano, hydroxyl, nitro, lower alkoxycarbonyl, halogen, lower alkoxy (C$_1$-C$_4$), lower perhaloalkoxy (C$_1$-C$_4$), unsubstituted amino, N-lower alkylamino (C$_1$-C$_4$), N-lower alkylamino carbonyl (C$_1$-C$_4$).

P is any protecting group for an amino group for a compound of Formula V and is selected from benzyl and t-butyloxy carbonyl groups.

The reaction of the compound of Formula V with a compound of Formula VI to give a compound of Formula VII is carried out in the presence of a condensing agent which is selected from the group consisting of 1-(3-dimethylamino propyl)-3-ethyl carbodiimide hydrochloride (EDC) and 1,8-diazabicyclo [5.4.0]undec-7-ene (DBU).

The reaction of the compound of Formula V with a compound of Formula VI to give a compound of Formula VII is carried out in a suitable solvent selected from the group consisting of N,N-dimethylformamide, dimethylsulfoxide, toluene, and xylene at a temperature ranging from about 0-140° C.

The deprotection of the compound of Formula VII to give a compound of Formula VIII is carried out with a deprotecting agent which is selected from the group consisting of palladium on carbon, trifluoroacetic acid (TFA) and hydrochloric acid.

The deprotection of the compound of Formula VII to give a compound of Formula VIII is carried out in a suitable organic solvent selected from the group consisting of methanol, ethanol, tetrahydrofuran and acetonitrile at temperatures ranging from about 10-50° C.

The N-alkylation or benzylation of the compound of Formula VIII to give a compound of Formula I is carried out with a suitable alkylating or benzylating agent, L-R$_4$ wherein L is any leaving group known in the art, preferably selected from halogen, O-mestyl and O-tosyl group.

The N-alkylation or benzylation of the compound of Formula VIII to give a compound of Formula I is carried out in a suitable organic solvent such as N,N-dimethylformamide dimethylsulfoxide, tetrahydrofuran and acetonitriie, at temperatures ranging from about 25-100° C.

Suitable salts of the compounds represented by the Formula I were prepared so as to solubilize the compound in aqueous medium for biological evaluations. Examples of such salts include pharmacologically acceptable salts such as inorganic acid salts (e.g. hydrochloride, hydrobromide, sulphate, nitrate and phosphorate), organic acid salts (e.g. acetate, tartrate, citrate, fumarate, maleate, toluenesulphonate and methanesulphonate). When carboxyl group is included in the Formula I as a substituent, it may be an alkali metal salt (e.g. sodium, potassium, calcium, magnesium, and the like). These salts may be prepared by the usual prior art techniques, such as treating the compound with an equivalent amount of inorganic or organic, acid or base in a suitable solvent.

The compound of Formula IV [Formula I, when W is (CH$_2$)$_p$ where p=0, X is no atom, Y is (CH$_2$)$_p$ where q=0, R$_6$=H, R$_7$=H, R$_2$=

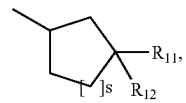

where R$_{11}$=H or F, R$_{12}$=F and s represents 1 to 2,

R$_1$=OH, Ar=phenyl] may be prepared by the following reaction sequence as depicted in Scheme-II Scheme-II

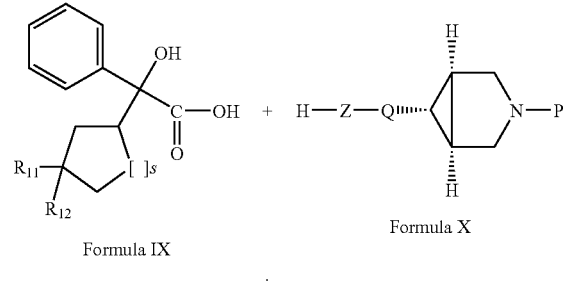

Formula IX

Formula X

Condensing agent

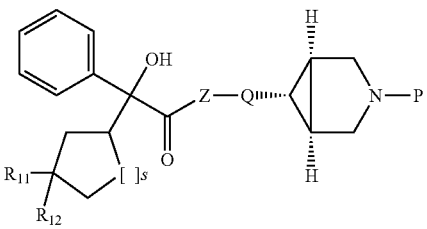

FORMULA XI

Deprotection

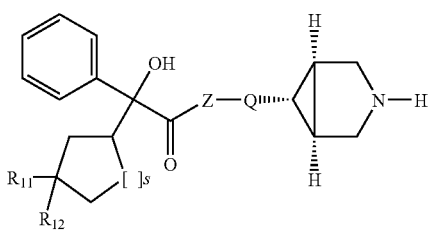

FORMULA XII

↓ N-Alkylation/Benzylation
  LR$_4$

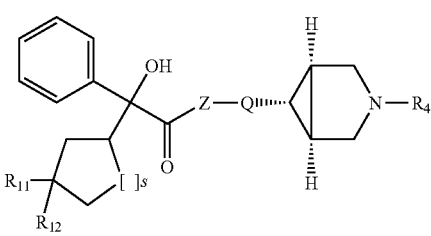

FORMULA IV

The preparation comprises condensing a compound of Formula IX with the compound of Formula X wherein Z, Q and s have the same meanings as defined earlier for Formula I, R$_{11}$ is hydrogen or fluoro and R$_{12}$ is fluoro. P is any protecting group for an amino group, in the presence of a condensing agent to give a protected compound of Formula XI which on deprotection in the presence of a deprotecting agent in an organic solvent gives an unprotected intermediate of Formula XIII which is finally N-alkylated or benzylated with a suitable alkylating or benzylating agent L-R$_4$ to give a compound of Formula IV wherein L is any leaving group and R$_4$ is defined above.

P is any protecting group for an amino group for a compound of Formula X and is selected from benzyl and t-butyloxy carbonyl groups.

The reaction of the compound of Formula IX with a compound of Formula X to give a compound of Formula XI is carried out in the presence of a condensing agent which is selected from the group consisting of 1-(3-dimethylaminopropyl)-3-ethyl carbodiimide hydrochloride (EDC) and 1,8-diazabicyclo [5.4.0]undec-7-ene (DBU).

The reaction of the compound of Formula IX with a compound of Formula X to give a compound of Formula XI is carried out in a suitable solvent selected from the group consisting of N,N-dimethylformamide, dimethylsulphoxide, toluene, and xylene at a temperature ranging from about 0-140° C.

The deprotection of the compound of Formula XI to give a compound of Formula XII is carried out in a suitable organic solvent selected from the group consisting of methanol, ethanol, tetrahydrofuran and acetonitrile at temperatures ranging from about 10-50° C.

The deprotection of the compound of Formula XI to give a compound of Formula XII is carried out with a deprotecting agent which is selected from the group consisting of palladium on carbon, trifluoroacetic acid (TFA) and hydrochloric acid.

The N-alkylation or benzylation of the compound of Formula XII to give a compound of Formula IV is carried out with a suitable alkylating or benzylating agent, L-R$_4$ wherein L is any leaving group known in the art, preferably selected from halogen, O-mestyl and O-tosyl group.

The N-alkylation or benzylation of the compound of Formula XII to give a compound of Formula IV is carried out in a suitable organic solvent such as N,N-dimethylformamide, dimethylsulphoxide, tetrahydrofuran and acetonitrile, at temperatures ranging from about 10-100° C.

Suitable salts of the compounds represented by the Formula IV were prepared so as to solubilize the compound in aqueous medium for biological evaluations. Examples of such salts include pharmacologically acceptable salts such as inorganic acid salts (e.g. hydrochloride, hydrobromide, sulphate, nitrate and phosphorate), organic acid salts (e.g. acetate, tartrate, citrate, fumarate, maleate, toluenesulphonate and methanesulphonate). When carboxyl group is included in the Formula I as a substituent, it may be an alkali metal salt (e.g. sodium, potassium, calcium, magnesium, and the like). These salts may be prepared by the usual prior art techniques, such as treating the compound with an equivalent amount of inorganic or organic, acid or base in a suitable solvent.

Acid of Formula IX can be synthesized following the procedures described in J. Org. Chem., 2001; 66:6775; Bioorg. and Med. Chem. 2000; 8:825 and references cited therein.

The compound of Formula IV [Formula I, when W is (CH$_2$)$_p$ where p=0, X is no atom, Y is (CH$_2$)$_p$ where q=0, R$_6$=R$_7$=H, R$_2$=

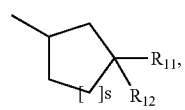

where R$_{11}$=H or F, R$_{12}$=F or sulphonamide and s represents 1 to 2, R$_1$=OH, Ar=phenyl) can also be prepared by reaction sequence as shown in Scheme-III.

Scheme-III

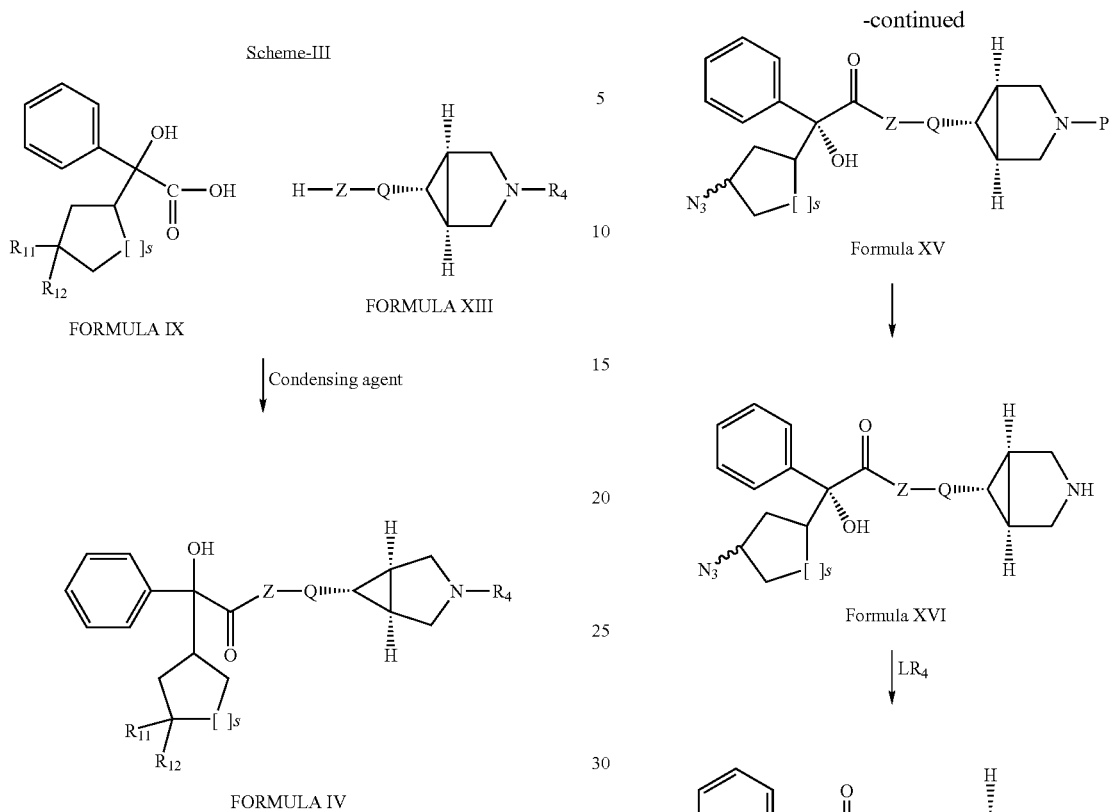

The preparation comprises condensing a compound of Formula IX with a compound of Formula XIII wherein Z, Q and $R_4$ have the same meanings as described earlier for Formula I.

The reaction of the compound of Formula IX with a compound of Formula XIII is carried out in the presence of a condensing agent which is selected from the group consisting of 1-(3-dimethylaminopropyl)-3-ethyl carbodiimide hydrochloride (EDC) and 1,8-diazabicyclo [5.4.0]undec-7-ene (DBU).

The reaction of the compound of Formula IX with a compound of Formula XIII is carried out in a suitable solvent selected from the group consisting of N,N-dimethylformamide, dimethyl sulfoxide, toluene, and xylene at a temperature ranging from about 0-140° C.

Scheme-IV

The compound of Formula IV (Formula I, when W is $(CH_2)_p$ where p=0, X is no atom, Y is $(CH_2)_p$ where q=0, $R_6=R_7=H$, $R_2=$

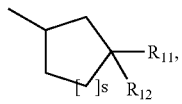

where $R_{11}$=H, $R_{12}$=substituted sulphonamide and s represents 1 to 2, $R_1$=OH, Ar=phenyl) of the present invention may be prepared by the reaction sequence as shown in Scheme-IV. The preparation comprises condensing a compound of Formula XIV with a compound of Formula X, where Z and Q have the same meanings as described earlier for Formula I to give a compound of Formula XV. The starting compound of Formula XIV was prepared by the known procedure described in *Bioorganic and Medicinal Chemistry*, 2000; 8:825.

The compound of Formula XVI is obtained by the deprotection of Formula XV in an organic solvent in the presence of a deprotecting agent. The intermediate of Formula XVI is finally N-alkylated or benzylated with suitable alkylating or benzylating agent L-$R_4$ to give a compound of Formula XVII wherein L is any leaving group and $R_4$ is the same as defined above.

P is any protecting group for an amino group for a compound of Formula X and is selected from benzyl and t-butyloxy carbonyl groups.

The reaction of the compound of Formula XIV with a compound of Formula X to give a compound of Formula XV is carried out in the presence of a condensing agent which is selected from the group consisting of 1-(3-dimethylaminopropyl)-3-ethyl carbodiimide hydrochloride (EDC) and 1,8-diazabicyclo[5.4.0]undec-7-ene (DBU).

The reaction of the compound of Formula XIV with a compound of Formula X to give a compound of Formula XV is carried out in a suitable solvent selected from the group consisting of N,N-dimethylformamide, dimethylsulphoxide, toluene, and xylene at a temperature ranging from about 0°-140° C.

The deprotection of the compound of Formula XV to give a compound of Formula XVI is carried out in a suitable solvent selected from the group consisting of methanol, ethanol, tetrahydrofuran and acetonitrile at temperature ranging from about 10°-50° C.

The N-alkylation or benzylation of the compound of Formula XVI to give a compound of Formula XVII is carried out with a suitable alkylating or benzylating agent, L-$R_4$ where L is any leaving group, known in the art, preferably selected from halogen, O-mestyl and O-tosyl group.

The N-alkylation or benzylation of the compound of Formula XVI to give a compound of Formula XVII is carried out in a suitable organic solvent such as N,N-dimethylformamide, dimethylsulfoxide, tetrahydrofuran and acetonitrile, at a temperature ranging from about 10°-100° C.

The reduction of the compound of Formula XVII to give a compound of Formula XVIII is carried out with triphenylphosphine in the presence of a suitable organic solvent such as tetrahydrofuran and water.

The compound XVIII on treatment with acid chlorides in a suitable solvent selected from the group consisting of dichloromethane, dichloroethane and chloroform gives the compound of Formula IV.

The acid chlorides may be selected from the group consisting of phenylacetylchloride, 4-nitrophenyl sulfonyl chloride, benzene sulfonyl chloride, benzyloxyacetyl chloride, 4-methoxy phenylsulfonyl chloride and 4-bromophenylsulfonyl chloride.

Suitable salts of the compounds represented by the Formula IV were prepared so as to solubilize the compound in aqueous medium for biological evaluations. Examples of such salts include pharmacologically acceptable salts such as inorganic acid salts (e.g. hydrochloride, hydrobromide, sulphate, nitrate and phosphorate), organic acid salts (e.g. acetate, tartrate, citrate, fumarate, maleate, toluenesulphonate and methanesulphonate). When carboxyl group is included in the Formula I as a substituent, it may be an alkali metal salt (e.g. sodium, potassium, calcium, magnesium, and the like). These salts may be prepared by the usual prior art techniques, such as treating the compound with an equivalent amount of inorganic or organic, acid or base in a suitable solvent.

In the above schemes, where specific bases, condensing agents, protecting groups, deprotecting agents, N-alkylating benzylating agents, solvents etc. mentioned, it is to be understood that other bases, condensing agents, protecting groups, deprotecting agents, N-alkylating, benzylating agents, solvents etc. known to those skilled in the art may be used. Similarly, the reaction temperature and duration may be adjusted according to the desired needs.

Preferred compounds according to the invention and capable of being produced by Scheme I-IV and are shown in Table 1 include:

| Compound No. | Chemical Name |
|---|---|
| 1A. | (2R)-(1α,5α,6α)-N-[3-benzyl-3-azabicyclo[3.1.0]hexyl-6-(aminomethyl)-yl]-2-[(1R or 1S)-3,3-difluorocyclopentyl]-2-hydroxy-2-phenylacetamide |
| 1B. | (2R)-(1α,5α,6α)-N-[3-benzyl-3-azabicyclo[3.1.0]hexyl-6-(aminomethyl)-yl]-2-[(1R or 1S)-3,3-difluorocyclopentyl]-2-hydroxy-2-phenylacetamide |
| 2. | (2R(1α,5α,6α)-N-[3-benzyl-3-azabicyclo[3.1.0]hexyl-6-(aminomethyl)-yl]-2-[(1R or 1S, 3R or 3S)-3-fluorocyclopentyl]-2-hydroxy-2-phenylacetamide |
| 3. | (2R or 2S)-(1α,5α,6α)-N-[3-benzyl-3-azabicyclo[3.1.0]hexyl-6-(aminomethyl)-yl]-2-[(1R or 1S)-3,3-difluorocyclopentyl]-2-hydroxy-2-phenyl acetamide |
| 4. | (2R or 2S)-(1α,5α,6α)-N-[3-benzyl-3-azabicyclo[3.1.0]hexyl-6-(aminomethyl)-yl]-2-[(1R or 1S, 3R or 3S)-3-fluorocyclopentyl]-2-hydroxy-2-phenyl acetamide |
| 5. | (2R)-(1α,5α,6α)-N-[3-benzyl-3-azabicyclo[3.1.0]hexyl-6-(aminomethyl)-yl]-2-[(1R or 1S, 3R or 3S)-3-phenyl acetylamino cyclopentyl]-2-hydroxy-2-phenylacetamide |

-continued

| Compound No. | Chemical Name |
|---|---|
| 6. | (2R)-(1α,5α,6α)-N-[3-benzyl-3-azabicyclo[3.1.0]hexyl-6-(aminomethyl)-yl]-2-[(1R or 1S, 3R or 3S)-3-(4-nitrophenyl)sulphonylamino cyclopentyl]-2-hydroxy-2-phenylacetamide |
| 7. | (2R)-(1α,5α,6α)-N-[3-benzyl-3-azabicyclo[3.1.0]hexyl-6-(aminomethyl)-yl]-2-[(1R or 1S, 3R or 3S)-3-phenylsulphonylamino cyclopentyl]-2-hydroxy-2-phenylacetamide |
| 8. | (2R)-(1α,5α,6α)-N-[3-benzyl-3-azabicyclo[3.1.0]hexyl-6-(aminomethyl)-yl]-2-[(1R or 1S, 3R or 3S)-3-benzyloxyacetylamino cyclopentyl]-2-hydroxy-2-phenylacetamide |
| 9. | (2R)-(1α,5α,6α)-N-[3-benzyl-3-azabicyclo[3.1.0]hexyl-6-(aminomethyl)-yl]-2-[(1R or 1S, 3R or 3S)-3-(4-methoxyphenyl) sulphonylamino cyclopentyl]-2-hydroxy-2-phenylacetamide |
| 10. | (2R)-(1α,5α,6α)-N-[3-benzyl-3-azabicyclo[3.1.0]hexyl-6-(aminomethyl)-yl]-2-[(1R or 1S, 3R or 3S)-3-(4-bromophenyl)sulphonylamino cyclopentyl]-2-hydroxy-2-phenylacetamide |

Table I

Formula-IV

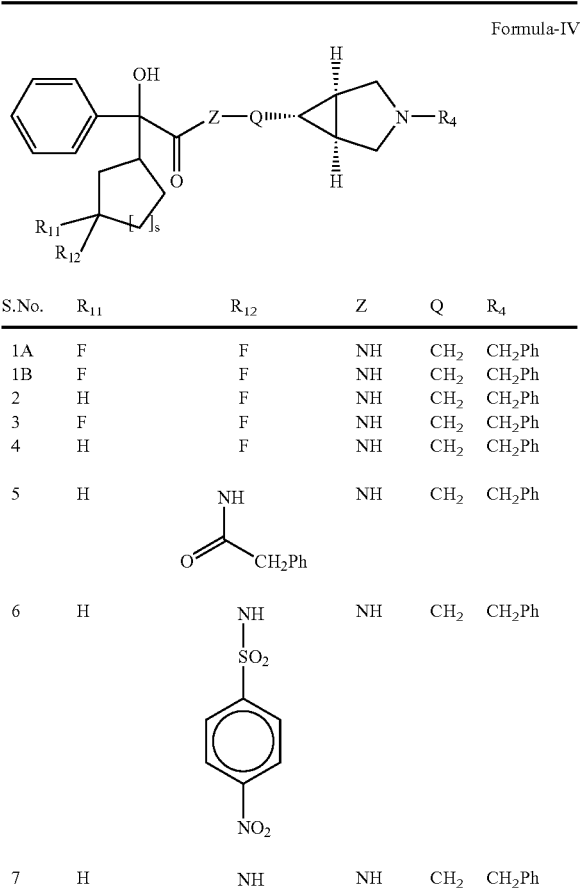

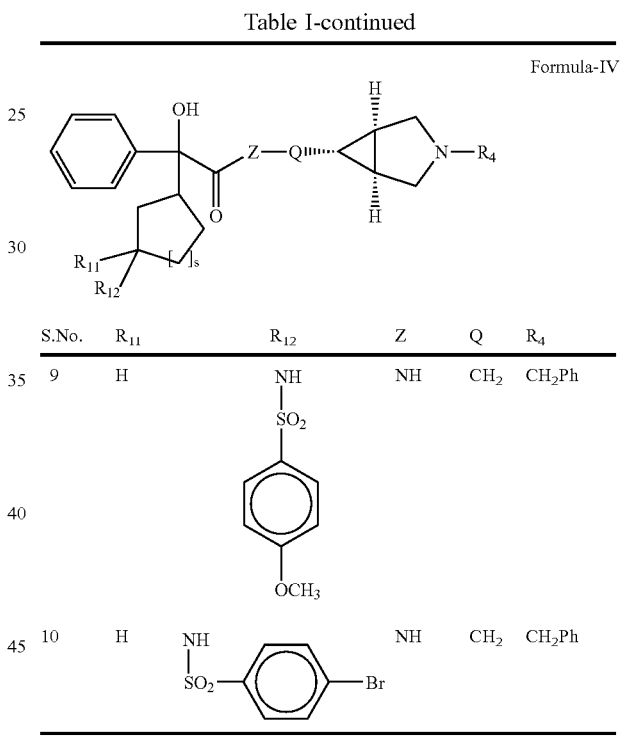

(Formula I, W is $(CH_2)p$ where p = 0, X is no atom, Y is $(CH_2)q$ where q = 0, $R_6 = R_7 = H$, $R_2 =$ cyclopentyl with $R_{11}$, $R_{12}$; s = 1, $R_1 = OH$, Ar = phenyl)

Because of their valuable pharmacological properties, the compounds of the present invention may be administered to an animal for treatment orally, or by parenteral route. The pharmaceutical compositions of the present invention are preferably produced and administered in dosage units, each unit containing a certain amount of at least one compound of the invention and/or at least one physiologically acceptable addition salt thereof. The dosage may be varied over extremely wide limits as the compounds are effective at low dosage levels and relatively free of toxicity. The compounds may be administered in the low micromolar concentration, which is therapeutically effective, and the dosage may be increased as desired up to the maximum dosage tolerated by the patient.

The present invention also includes within its scope prodrugs of the compounds of Formula I, II, III and IV. In general, such prodrugs will be functional derivatives of these compounds, which readily are converted in vivo into the defined compounds. Conventional procedures for the selection and preparation of suitable prodrugs are known.

The present invention also includes the enantiomers, diastereomers, N-oxides, polymorphs, solvates and pharmaceutically acceptable salts of these compounds as well as metabolites having the same type of activity. The present invention further includes the pharmaceutical composition comprising the molecules of Formulae I, II, III and IV or prodrugs, metabolites, enantiomers, diastereomers, N-oxides, polymorphs, solvates or pharmaceutically acceptable salts thereof, in combination with pharmaceutically acceptable carrier and optionally included excipient.

The examples mentioned below demonstrate the general synthetic procedure as well as the specific preparation of the preferred compound. The examples are provided to illustrate the details of the invention and should not be constrained to limit the scope of the present invention.

EXPERIMENTAL DETAILS

Various solvents, such as acetone, methanol, pyridine, ether, tetrahydrofuran, hexane, and dichloromethane, were dried using various drying agents according to the procedure described in the literature. IR spectrum were recorded as nujol mulls or a thin neat film on a Perkin Elmer Paragon Instrument and Nuclear Magnetic Resonance (NMR) were recorded on a Varian XL-300 MHz instrument using tetramethylsilane as an internal standard.

EXAMPLE 1

Preparation of (2R)-(1α,5α,6α)-N-3-benzyl-3-azabicyclo[3.1.0]hexyl-6-(aminomethyl)-yl]-2-[(1R or 1S)-3,3-difluorocyclopentyl]-2-hydroxy-2-phenylacetamide (Compound Nos. 1A and 1B)

Step a: Preparation of (2R,5R)-2-tert-butyl-5-phenyl-1,3-dioxalan-4-one

The compound was synthesized following the procedure described in *J. Org. Chem.* 2000; 65:6283.

Step b: Preparation of (2R,5R)-2-tert-butyl-5-[(1R or 1S)-3-oxocyclopentyl]-5-phenyl-1,3-dioxalan-4-one To a suspension of the compound obtained at step a (1.36 mmol) in tetrahydrofuran (12 ml) was added lithium diisopropyl amide (LDA) in tetrahydrofuran (1.5 mmol) drop wise at −78° C. under nitrogen atmosphere. The reaction mixture was stirred at the same temperature for 2 hours. A solution of 2-cyclopenten-1-one (1.52 mmol) in tetrahydrofuran (2 ml) was added to the reaction mixture dropwise and stirred for additional 3 hours. The reaction mixture was quenched with saturated aqueous ammonium chloride solution and extracted with ethyl acetate. The organic layer was dried and the residue obtained after removing the solvents in vacuo was purified by column chromatography (100-200 mesh silica gel). The product was eluted with 10% ethylacetate-hexane mixture.

$^1$HNMR(CDCl$_3$) δ-values: 7.70-7.26 (m,5 Ar—H), 5.43-5.37 (d, 1H), 2.91-2.88 (m,1H), 2.37-1.77 (m, 6H), 0.92 (s, 9H) IR(DCM): 1791 and 1746 cm$^{-1}$ Step c: Preparation of (2R,5R)-2-tert-butyl-5-[(1R or 1S)-3,3-difluorocyclopentyl]-5-phenyl-1,3-dioxalan-4-one To a solution of the compound of step-b (1 mmol) in chloroform (15 ml) was added diethyl amino sulphur trifluoride (DAST), (3.3 mmol) at 0° C. under nitrogen atmosphere. The reaction mixture was stirred at the same temperature for 30 minutes and then at room temperature for 3 days. After being cooled to 0° C., the reaction mixture (RM) was quenched carefully by adding water. The organic layer was separated and the aqueous layer extracted with chloroform. The combined organic layers were dried and the residue obtained after removing the solvent was purified by column chromatography (100-200 mesh size silica gel) eluting the compound with 5% ethylacetate-hexane mixture.

$^1$HNMR(CDCl$_3$) δ-values: 7.73-7.35 (m, 5 Ar—H), 5.49 (s, 1H), 2.86-2.82 (m, 1H), 2.27-1.80 (m, 6H), 0.98 (s,H) IR(DCM): 1793 cm$^{-1}$ Step d: Preparation of (2R) [(1S or 1 R)-3,3-difluorocyclopentyl]-2-hydroxy-2-phenylaceticacid The solution of the compound of step-c (1 mmol) in methanol (10 ml) was stirred with 3N aqueous sodium hydroxide solution for overnight at room temperature. The reaction mixture was concentrated under reduced pressure. The residue was diluted with water and extracted with dichloromethane. The aqueous layer was acidified with conc. hydrochloric acid and extracted with ethylacetate. The organic layer was dried and concentrated under reduced pressure to give the product.

m.pt.:123° C. $^1$HNMR(CDCl$_3$) δ-values: 7.69-7.37(m, 5 Ar—H), 3.29-3.20(m, 1H), 2.39-1.68 (m, 6H)

Step e: Preparation of (1α,5α,6α)-6-aminomethyl-3-benzyl-3-azabicyclo[3.1.0]hexane The compound was synthesized as per the procedure of EP0413455A2.

Step f: Preparation of (2R)-(1α,5α,6α)-N-[3-benzyl-3-azabicyclo[3.1.0]hexyl-6-(aminomethyl)-yl]-2-[(1R or 1S)-3,3-difluorocyclopentyl]-2-hydroxy-2-phenylacetamide A solution of (2R)-[(1S or 1R)-3,3-difluorocyclopentyl]-2-hydroxy-2-phenylacetic acid (1 mmol) and (1α,5α,6α)-6-aminomethyl-3-benzyl-3-azabicyclo[3.1.0]hexane(1.1 mmol) in DMF (10 ml) was cooled to 0° C. 1-Hydroxybenzotriazole (HOBT, 1.1 mmol) and N-methylmorpholine (NMM, 2 mmol) were added to the reaction mixture and reaction mixture stirred for 1 hour at 0° C. 1-(3-dimethylaminopropyl)-3-ethyl carbodiimide (EDC.HCl) (1 mmol) was added to the reaction mixture at 0° C. The reaction mixture was stirred at 0° C. for 1 hour 30 minutes and then at room temperature for overnight. The reaction mixture was poured into saturated sodium bicarbonate solution and extracted with ethylacetate. The organic layer was washed with water and dried. The residue obtained after the removal of solvent was purified by column chromatography (100-200 mesh silica gel) eluting the compounds with 25-30% ethylacetate-hexane mixture.

Compound-1A:

¹HNMR (CDCl₃) δ-values: 7.58-7.22 (m, 10 ArH), 6.33 (bs, 1H), 3.56 (s, 2H), 3.30 (m, 1H), 3.05-2.89 (m, 4H), 2.32-2.29 (m, 2H), 2.16-1.21 (m, 9H) IR (KBr): 1654 cm⁻¹

Compound-1B:

¹HNMR (CDCl₃) δ-values: 7.58-7.22 (m, 10 ArH), 6.39 (bs, 1H), 3.56 (s, 2H), 3.48 (m, 1H), 3.48 (m, 1H), 3.07-2.89 (m, 4H), 2.32-2.29 (m, 2H), 2.16-1.21 (m, 9H) IR (KBr): 1652 cm⁻¹

Compound 1A and Compound 1 B are a Pair of Diastereomers.

EXAMPLE 2

Preparation of (2R)-(1α,5α,6α)-N-[3-benzyl-3-azabicyclo[3.1.0]hexyl-6-(aminomethyl)-yl]-2-[(1R or 1S, 3R or 3S)-3-fluorocyclopentyl]-2-hydroxy-2-phenyl acetamide (Compound No. 2)

Step-a: Preparation of (2R)-2-tert-butyl-5-[(1R or 1S, 3R or 3S)-3-hydroxy cyclopentyl]-5-phenyl-1,3-dioxalan-4-one To a solution of (2R,5R)-2-tert-butyl-5-[(1R or 1S)-3-oxocyclopentyl]-5-phenyl-1,3-dioxalan-4-one (1 mmol) in methanol (10 ml) cooled to 0° C., sodium borohydride (2 mmol) was added in small lots with stirring. The reaction mixture was stirred at 0° C. for 1 hr. It was concentrated under reduced pressure and the residue diluted with water and extracted with ethylacetate. The organic layer was dried and the residue obtained after the removal of solvents was purified by column chromatography (100-200 mesh silica gel) eluting the compound with 20% ethylacetate-hexane mixture.

¹HNMR(CDCl₃) δ-values: 7.68-7.29 (m, 5H, ArH), 5.45 (d, 1H), 4.30 (m, 1H), 3.25 (m, 1H), 2.65-2.63 (m, 1H), 1.80-1.63 (m, 6H), 0.92 (s, 9H) IR(DCM): 1789 cm⁻¹, 3386 cm⁻¹

Step-b: Preparation of (2R)-2-tert-butyl-5-[1R or 1S, 3R or 3S]-3-fluorocyclopentyl]-5-phenyl-1,3-dioxolan-4-one The solution of the compound of step-a (1 mmol) in chloroform (10 ml) was cooled to 0° C. and DAST (1.5 mmol) was added dropwise under nitrogen atmosphere. The reaction mixture (RM) was stirred at 0° C. for 30 minutes and then at room temperature for 3 days. The RM was cooled and carefully quenched with aqueous ammonium chloride solution. The organic layer was separated and aqueous layer extracted with ethylacetate. The combined organic layer was dried and residue obtained after removing the solvents was purified by column chromatography (100-200 mesh, silica gel) eluting the compound with 5% ethylacetate-hexane mixture.

¹HNMR(CDCl₃) δ-values: 7.68-7.28 (m, 5H, Ar—H), 5.46 (d, 1H), 5.39 (m, 1H), 2.90 (m, 1H), 1.98-1.25 (m, 6H), 0.93 (s, 9H)

Step-c: Preparation of (2R)-[(1R or 1S, 3R or 3S]-3-fluorocyclopentyl]-2-hydroxy-2-phenylacetic acid The compound was synthesized following the procedure of Example 1, step-d using (2R,5R)-2-tert-butyl-5-[(1R or 1S, 3R or 3S)-3-fluorocyclopentyl]-5-phenyl-1,3-dioxalan-4-one instead of (2R,5R)-2-tert-butyl-5-[(1R or 1S)-3,3-difluorocyclopentyl]-5-phenyl-1,3-dioxolan-4-one.

¹HNMR(CDCl₃) δ-values: 7.66-7.27 (m, 5 Ar—H), 5.30-5.00 (m, H), 3.32-3.16 (m, 1H), 2.05-1.26 (m, 6H). IR(DCM): 1710 cm⁻¹

Step-d: Preparation of (2R)-(1α,5α,6α)-N-[3-benzyl-3-azabicyclo[3.1.0]hexyl-6-(aminomethyl)-yl]-2-[1R or 1S, 3R or 3S]-3-fluorocyclopentyl]-2-hydroxy-2-phenylacetamide The compound was synthesized following the procedure of Example 1, step-f, using (2R)-[(1R or 1S, 3R or 3S-3-fluorocyclopentyl]-2-hydroxy-2-phenyl acetic acid instead of (2R)-[(1R or 1S)-3,3-difluorocyclopentyl]-2-hydroxy-2-phenylacetic acid.

¹HNMR(CDCl₃) δ-values: 7.71-7.24 (m, 10H, Ar—H), 6.04 (b, 1H), 5.21-5.10 (m, 1H), 3.55 (s, 2H), 3.26-2.86 (m, 5H), 2.31-2.28 (m, 2H), 2.00-1.20 (m, 9).

EXAMPLE 3

Preparation of (2R or 2S)-(1α,5α,6α)-N-[3-benzyl-3-azabicyclo[3.1.0]hexyl-6-(aminomethyl)-yl]-2-[(1R or 1S)-3,3-difluorocyclopentyl]-2-hydroxy-2-phenyl acetamide (Compound No. 3)

Step a: Preparation of (2R or 2S,5R or 5S)-2-tert-butyl-5-phenyl-1,3-dioxalan-4-one The compound was synthesized as per the procedure described in J. Org. Chem. 2000; 65:6283, using DL-Mandelic acid instead of R-(–)-Mandelic acid.

Step b: Preparation of (2R or 2S,5R or 5S)-2-tert-butyl-5-[(1R or 1S)-3-oxocyclopentyl]-5-phenyl-1, 3-dioxalan-4-one The compound was synthesized following the procedure of Example 1, step-b, using (2R or 2S, 5R or 5S)-2-tert-butyl-5-phenyl-1,3-dioxalan-4-one instead of (2R,5R)-2-tert-butyl-5-phenyl-1,3-dioxalan-4-one.

Step c: Preparation of (2R or 2S, 5R or 5S)-2-tert-butyl-5-[(1R or 1S)-3,3-difluorocyclopentyl]-5-phenyl-1,3-dioxalan-4-one The compound was prepared following the procedure of Example 1, step-c, using (2R or 2S, 5R or 5S)-2-tert-butyl-5-[(1R or 1S)-3-oxocyclopentyl]-5-phenyl-1,3-dioxalan-4-one instead of (2R,5R)-2-tert-butyl-5-[(1R or 1S)-3-oxocyclopentyl]-5-phenyl-1,3-dioxalan-4-one.

¹HNMR(CDCl₃) δ-values: 7.67-7.29(m, 5 Ar—H), 5.34 (s, 1H), 2.80-2.76(m, 1H), 2.23-1.70(m, 6H), 0.92(s, 9H)

Step d: Preparation of (2R or 2S,5R or 5S)-2-[(1R or 1S)-3,3-difluorocyclopentyl]-2-hydroxy-2-phenylacetic acid The compound was synthesized following the procedure of Example 1, step-d-d, using (2R or 2S, 5R or 5S)-2-tert-butyl-5-[(1R or 1S)-3,3-difluorocyclopentyi]-5-phenyl-1,3-dioxalan-4-one instead of (2R,5R)-2-tert-butyl-5-[(1R or 1S)-3,3-difluorocyclopentyl]-5-phenyl-1,3-dioxalan-4-one.

¹HNMR(CDCl₃) δ-values: 7.65-7.31 (m, 5 Ar—H), 3.23-3.14(m, 1H), 2.25-1.62(m 6H) IR (KBr): 1724 cm⁻¹

Step e: Preparation of (2R or 2S)-(1α,5α,6α)-N-[3-benzyl-3-azabicyclo[3.1.0]hexyl-6-(aminomethyly)-yl]-2-[(1R or 1S)-3,3-difluorocyclopentyl]-2-hydroxy-2-phenyl acetamide The compound was synthesized following the procedure of Example 1, step-f, using (2R or 2S, 5R or 5S)-2-[(1R or 1S)-3,3-difluorocyclopentyl]-2-hydroxy-2-phenylacetic acid instead of (2R,5R)-2-[(1R or 1S)-3,3-difluorocyclopentyl]-2-hydroxy-2-phenylacetic acid.

$^1$HNMR(CDCl$_3$) δ-values: 7.58-7.23 (m, 10 Ar—H), 6.33 (bs, 1H), 3.56 (s, 2H), 3.47 (s, 1H), 3.33-3.25(m, 1H), 3.05-2.88(m, 4H), 2.31-2.28(m, 2H), 2.21-1.66(m, 9H) IR (KBr): 1652 cm$^{-1}$ HPLC: Single compound (Diastereomers could not be separated).

EXAMPLE 4

Preparation of (2R or 2S)-(1α,5α,6α)-N-[3-benzyl-3-azabicyclo[3.1.0]hexyl-6-(aminomethyl)-yl]-2-[(1R or 1S, 3R or 3S)-3-fluorocyclopentyl]-2-hydroxy-2-phenyl acetamide (Compound No. 4)

Step a: Preparation of (2R or 2S, 5R or 5S)-2-tert-butyl-5-[(1R or 1S, 3R or 3)-3-hydroxycyclopentyl]-5-phenyl-1,3-dioxalan-4-one To a solution of (2R or 2S, 5R or 5S)-2-tert-butyl-5-[(1R or 1S)-3-oxocyclopentyl]-5-phenyl-1,3-dioxalan-4-one (1 mmol) in methanol (10 ml) cooled to 0° C. Sodium borohydride (2 mmol) was added in small lots with stirring. The RM was stirred at 0° C. for 1 hour. It was concentrated under reduced pressure and the residue diluted with water and extracted with EtOAc. The organic layer was dried and the residue obtained after removal of solvents was purified by column chromatography (100-200 mesh silicagel) eluting the compound with 20% EtOAc-hexane mixture.

$^1$HNMR(CDCl$_3$) δ-values: 7.68-7.29(m, 5 Ar—H), 5.45 (d, 1H), 4.3(m, 1H), −3.25(m, 1H), 2.65-2.63(m, 1H), 1.80-1.63(m, 6H), 0.92(s, 9H) IR (DCM): 1789 cm$^{-1}$, 3386 cm$^{-1}$ Step b: Preparation of (2R or 2S, 5R or 5S)-2-tert-butyl-5-[(1R or 1S, 3R or 3S)-3-fluorocyclopentyl]-5-phenyl-1,3-dioxalan-4-one A solution of the compound of step-a (1 mmol) in chloroform (10 ml) was cooled to 0° C. and DAST (1.5 mmol) was added dropwise under nitrogen atmosphere. The RM was stirred at 0° C. for 30 minutes and then at room temperature for 3 days. The RM was cooled and quenched with aqueous ammonium chloride solution. The organic layer was separated and aqueous layer extracted with EtOAc. The combined organic layers were dried and the residue obtained after removing the solvents was purified by column chromatography (100-200 mesh size, silica gel) eluting the compound with 5% EtOAc-hexane mixture.

$^1$HNMR(CDCl$_3$) δ-values: 7.69-7.23(m, 5 Ar—H), 5.42 (d, 1H), 5.28-5.16(m, 1H), 2.92-2.86(m, 1H), 1.97-1.24(m, 6H), 0.90(s, 9H) IR (DCM): 1791 cm$^{-1}$ Step c: Preparation of (2R or 2S)-[(1R or 1S, 3R or 3S)-3-fluorocyclopentyl]-2-hydroxy-2-phenyl acetic acid The compound was synthesized following the procedure of Example 1, step-d, using (2R or 2S, 5R or 5S)-2-tert-butyl-5-[(1R or 1S, 3R or 3S)-3-fluorocyclopentyl]-5-phenyl-1,3-dioxalan-4-one instead of (2R,5R)-2-tert-butyl-5-[(1R or 1S)-3,3-difluorocyclopentyl]-5-phenyl-1,3-dioxalan-4-one $^1$HNMR(CDCl$_3$) δ-values: 7.66-7.25(m, 5 Ar—H), 5.30-4.99(m, 1H), 3.81-3.76(m, 1H), 2.01-1.64(m, 6H) IR (KBr): 1722 cm$^{-1}$ Step d: Preparation of (2R or 2S)-(1α,5α,6α)-N-[3-benzyl-3-azabicyclo[3.1.0]hexyl-6-(aminomethyl)-yl]-2-[(1R or 1S, 3R or 3S)-3-fluorocyclopentyl]-2-hydroxy-2-phenyl acetamide The compound was synthesized following the procedure of Example 1, step-f, using (2R or 2S)-[(1R or 1S, 3R or 3S)-3-fluorocyclopentyl]-2-hydroxy-2-phenyl acetic acid instead of (2R)-[(1R or 1S)-3,3-difluorocyclopentyl]-2-hydroxy-2-phenylacetic acid.

$^1$HNMR(CDCl$_3$) δ-values: 7.66-7.25(m, 10 Ar—H), 6.05 (bs, 1H), 5.30-5.03 (m, 1H), 3.98 (s, 2H), 3.56-2.87 (m, 5H), 2.31-2.28(m, 2H), 1.97-1.11(m, 9H) IR (DCM): 1652 cm$^{-1}$

EXAMPLE 5

Preparation of (2R)-(1α,5α,6α)-N-[3-benzyl-3-azabicyclo[3.1.0]hexyl-6-(aminomethyl)-yl]-2-[(1R or 1S, 3R or 3S)-3-phenylacetylamino cyclopentyl]-2-hydroxy-2-phenylacetamide (Compound No. 5)

Step a: Preparation of (2R,5R)-2-tert-butyl-5-[(1R or 1S, 3R or 3S)-3-azidocyclopentyl]-5-phenyl-1,3-dioxalan-4-one To a solution of (2R,5R)-2-tert-butyl-5-[(1R or 1S, 3R or 3S)-3-hydroxycyclopentyl]-5-phenyl-1,3-dioxalan-4-one (1 mmol) and triethylamine (2.5 mmol) in ethyl acetate (10 ml) was added methane sulphonyl chloride (2 mmol) and the RM stirred for 1 hour at 0° C. and then at room temperature for 1 hour. Saturated aq. sodium bicarbonate solution was added, the organic layer separated and washed with water The organic layer was dried and the residue obtained after the removal of solvent was used as such for the next step.

The residue (1 mmol) was dissolved in DMF (10 ml) and to it sodium azide (4 mmol) was added. The RM was heated at 90-95° C. for 4 hours, cooled to room temperature, diluted with water and extracted with EtOAc. The organic layer was dried and the residue obtained after removing the solvent was used as such.

$^1$HNMR(CDCl$_3$) δ-values: 7.66-7.26 (m, 5 Ar—H), 5.40 (s, 1H), 4.00-3.97 (m, 1H), 2.83-2.78 (m, 1H), 1.80-1.04 (m, 6H), 0.93 (s, 9H) IR (DCM): 1791 and 2099 cm$^{-1}$ Step b: Preparation of (2R)-[(1R or 1S, 3R or 3S)-3-azidocyclopentyl]-2-hydroxy-2-phenyl acetic acid To a solution of the compound of step-a (1 mmol) in 10 ml of methanol, 3N aq. sodium hydroxide solution was added and the RM stirred for overnight at room temperature. The RM was concentrated under reduced pressure, diluted with water and extracted with dichloromethane. The aqueous layer was acidified with 1N hydrochloric acid and extracted with chloroform. The organic layer was washed with water, dried and concentrated under reduced pressure to give the required product.

$^1$HNMR(CDCl$_3$) δ-values: 7.65-7.26(m, 5 Ar—H), 4.07-3.97 (m, 1H), 3.22-3.14 (m, 1H), 1.89-1.25 (m, 6H) IR (DCM): 1712 and 2102 cm$^{-1}$

Step c: Preparation of (2R)-(1α,5α,6α)-N-[3-benzyl-3-azabicyclo[3.1.0]hexyl-6-(aminomethyl)-yl]-2-[(1R or 1S, 3R or 3S)-3-azidocyclopentyl]-2-hydroxy-2-phenylacetamide To a solution of the compound of step-b (1 mmol) and (1α,5α,6α)-6-aminomethyl-3-benzyl-3-azabicyclo[3.1.0]hexane (0.9 mmol) in DMF (10 ml) was added NMM (2 mmol) and HOBT (1.1 mmol) at 0° C. and stirred at the same temperature for 1 hour. EDC.HCl (1 mmol) was then added and the RM stirred for 1 hour at 0° C. and then at room temperature for 4 days. The RM was poured into water and extracted with EtOAc. The organic layer was dried and the residue obtained after the removal of solvent was purified by column chromatography.

$^1$HNMR(CDCl$_3$) δ-values: 7.74-7.22 (m, 10 Ar—H), 6.07 (bs, 1H), 3.98-3.96 (m, 1), 3.55 (s, 2H), 3.04-2.99 (m, 5H), 2.31-2.28 (m, 2H), 1.76-1.19 (m, 9H) IR (DCM): 1654 and 2097 cm$^{-1}$

Step-d: Preparation of (2R)-(1α,5α,6α)-N-[3-benzyl-3-azabicyclo[3.1.0]hexyl-6-(aminomethyl)-yl]-2-[(1R or 1S, 3R or 3S)-3-aminocyclopentyl]-2-hydroxy-2-phenyl acetamide To a solution of the compound of, step-c, (9 mmol) in a mixture of THF and water (75+15 ml), triphenyl phosphine (27 mmol) was added and the RM refluxed for 18 hours. The RM was cooled to room temperature, solvent removed in vacuo and the residue diluted with water. The pH was made acidic with 1N HCl and the RM extracted with chloroform. The aqueous layer was then made basic with 1N sodium hydroxide solution and extracted with chloroform. The organic layer was washed with water, dried and concentrated under reduced pressure. The residue was used as such for the next step.

Step e: Preparation of (2R)-(1α,5α,6α)-N-[3-benzyl-3-azabicyclo[3.1.0]hexyl-6-(aminomethyl)-yl]-2-[(1R or 1S, 3R or 3S)$_3$-phenylacetylamino cydopentyl]-2-hydroxy-2-phenylacetamide To a solution of the compound of step-d, triethylamine (2.2 mmol), dimethyl aminopyridine (1 mg) in chloroform was added phenylacetyl chloride (2.2 mmol) at 0° C. The RM was stirred for overnight at room temperature. Aqueous sodium hydroxide was added and the organic layer separated. The organic layer was washed with water, dried and the solvent removed in vacuo. The residue was purified by column chromatography.

m.pt.:56-61° C. IR (DCM): 1650 cm$^{-1}$

EXAMPLE 6

Preparation of (2R)-(1α,5α,6α)-N-[3-benzyl-3-azabicyclo[3.1.0]hexyl-6-(aminomethyl)-yl]-2-[(1R or 1S, 3R or 3S)-34(4-nitrophenyl)sulphonylaminocyclopentyl]-2-hydroxy-2-phenylacetamide (Compound No. 6)

The compound was synthesized following the procedure of Example 5, step-e, using 4-nitrophenyl sulphonyl chloride instead of phenylacetyl chloride.

m.pt.:67-71° C. $^1$HNMR(CDCl$_3$) δ-values: 8.35-8.26 (m, 2 ArH), 8.06-7.97 (m, 2 ArH), 7.51-7.26 (m, 10 ArH), 6.34 (bs, 1H), 3.67-2.90 (m, 9H), 2.35-1.15 (m, 10H) IR (KBr): 1652 and 1529 cm$^{-1}$

EXAMPLE 7

Preparation of (2R)-(1α,5α,6α)-N-[3-benzyl-3-azabicyclo[3.1.0]hexyl-6-(aminomethyl)-yl]-2-[(1R or 1S, 3R or 3S)-3-phenylsulphonylaminocyclopentyl]-2-hydroxy-2-phenylacetamide (Compound No. 7)

The compound was synthesized following the procedure of Example 5, step-e, using benzene sulphonyl chloride instead of phenylacetyl chloride.

m.pt.:52-56° C. $^1$HNMR(CDCl$_3$) δ-values: 7.88-7.26 (m, 15 ArH), 6.26 (bs, 1H), 3.67-2.86(m, 9H), 2.35-1.10(m, 12H) IR (KBr): 1654 cm$^{-1}$

EXAMPLE 8

Preparation of (2R)-(1α,5α,6α)-N-[3-benzyl-3-azabicyclo[3.1.0]hexyl-6-(aminomethyl)-yl]-2[(1R or 1S, 3R or 3S)-3-benzyloxyacetylaminocyclopentyl]-2-hydroxy-2-phenylacetamide (Compound No. 8)

The compound was synthesized following the procedure of Example 5, step-e, using benzyloxyacetyl chloride instead of phenylacetyl chloride.

$^1$HNMR(CDCl$_3$) δ-values: 7.59-7.26 (m, 15 ArH), 6.26 (bs, 1H), 4.55 (d, 2H), 3.95-3.56 (m, 4H), 3.28 (s, 2H), 3.04-2.90 (m, 4H), 2.32-2.29 (m, 2H), 2.05-1.13 (m, 10H) IR (DCM): 1655 cm$^{-1}$

EXAMPLE 9

Preparation of (2R)-(1α,α,6α)-N-[3-benzyl-3-azabicyclo[3.1.0]hexyl-6-(aminomethyl)-yl]-2-[(1R or 1S, 3R or 3S)-3-(4-methoxyphenyl)sulphonylamino cyclo pentyl]-2-hydroxy-2-phenylacetamide (Compound No. 9)

The compound was synthesized following the procedure of Example 5, step-e, using 4-methoxyphenyl sulphonyl chloride instead of phenylacetyl chloride.

$^1$HNMR(CDCl$_3$) δ-values: 7.85-6.96(m, 14 ArH), 6.30 (bs, 1H),3.89(s, 3H), 3.6 (s, 2H), 3.05-2.91 (m, 5H), 2.36-2.34 (m, 2H), 1.83-0.93 (m, 10H) IR (DCM): 1661 cm$^{-1}$

EXAMPLE 10

Preparation of (2R)-(1α,5α,6α)-N-[3-benzyl-3-azabicyclo[3.1.0]hexyl-6-(aminomethyl)-yl]-2-[(1R or 1S, 3R or 3S)-3-(4-bromophenyl)sulphonylaminocyclopentyl]-2-hydroxy-2-phenylacetamide (Compound No. 10)

The compound was synthesized following the procedure of Example 5, step-e, using 4-bromophenyl sulphonyl chloride instead of phenylacetyl chloride.

$^1$HNMR(CDCl$_3$) δ-values: 7.73-7.26 (m, 14 ArH), 6.26 (bs, 1H), 3.57-2.86 (m, 7H), 2.33-2.29(m, 2H), 1.85-1.19(m, 10H) IR (DCM): 1651 cm$^{-1}$

BIOLOGICAL ACTIVITY

Radioligand Binding Assays:

The affinity of test compounds for M$_2$ and M$_3$ muscarinic receptor subtypes was determined by [$^3$H]-N-methylscopolamine binding studies using rat heart and submandibular gland respectively as described by Moriya et al., (Life Sci, 1999, 64(25):2351-2358) with minor modifications.

Membrane preparation: Submandibular glands and heart were isolated and placed in ice cold homogenising buffer (HEPES 20 mM, 10 mM EDTA, pH 7.4) immediately after sacrifice. The tissues were homogenised in 10 volumes of homogenising buffer and the homogenate was filtered through two layers of wet gauze and filtrate was centrifuged at 500 g for 10 min. The supernatant was subsequently centrifuged at 40,000 g for 20 min. The pellet thus obtained was resuspended in same volume of assay buffer (HEPES 20 mM, EDTA 5 mM, pH 7.4) and were stored at −70° C. until the time of assay.

Ligand binding assay: The compounds were dissolved and diluted in DMSO. The membrane homogenates (150-250 µg protein) were incubated in 250 µl of assay buffer (HEPES 20 mM, pH 7.4) at 24-25° C. for 3 h. Non-specific binding was determined in the presence of 1 µM atropine. The incubation was terminated by vacuum filtration over GF/B fiber filters(Wallac). The filters were then washed with ice cold 50 mM Tris HCl buffer (pH 7.4). The filter mats were dried and bound radioactivity retained on filters was counted. The $IC_{50}$ & Kd were estimated by using the non-linear curve fitting program using G Pad Prism software. The value of inhibition constant Ki was calculated from competitive binding studies by using Cheng & Prusoff equation (*Biochem Pharmacol*, 1973, 22: 3099-3108), $Ki=IC_{50}/(1+L/Kd)$, where L is the concentration of [$^3$H]NMS used in the particular experiment.

Functional Experiments Using Isolated Rat Bladder:

Methodology:

Animals were euthanized by overdose of urethane and whole bladder was isolated and removed rapidly and placed in ice cold Tyrode buffer with the following composition (mMol/L) NaCl 137; KCl 2.7; $CaCl_2$ 1.8; $MgCl_2$ 0.1; $NaHCO_3$ 11.9; $NaH_2PO_4$ 0.4; Glucose 5.55 and continuously gassed with 95% $O_2$ and 5% $CO_2$.

The bladder was cut into longitudinal strips (3 mm wide and 5-6 mm long) and mounted in 10 ml organ baths at 30° C., with one end connected to the base of the tissue holder and the other end connected to a polygraph through a force displacement transducer. Each tissue was maintained at a constant basal tension of 2 g and allowed to equilibrate for 1 hour during which the PSS was changed every 15 min. At the end of equilibration period the stabilization of the tissue contractile response was assessed with 1 µmol/L of Carbachol consecutively for 2-3 times. Subsequently a cumulative concentration response curve to carbachol ($10^{-9}$ mol/L to $3 \times 10^{-5}$ mol/L) was obtained. After several washes, once the baseline was achieved, cumulative concentration response curve was obtained in presence of NCE (NCE added 20 min. prior to the second CRC).

The contractile results were expressed as % of control E max. ED50 values were calculated by fitting a non-linear regression curve (Graph Pad Prism). pKB values were calculated by the formula pKB=−log [(molar concentration of antagonist/(dose ratio-1))]

where, dose ratio=ED50 in the presence of antagonist/ED50 in the absence of antagonist.

The result of the in-vitro test are listed in Table II.

In-Vitro Tests

TABLE II

| | Receptor Binding Assay | | |
|---|---|---|---|
| | $M_2$ pKi | $M_3$ pKi | Functional Assay $pK_B$ |
| Compound No. 1A | 6.87 | 8.25 | 9.1 ± 0.2 |
| Compound No. 1B | 6.64 | 8.21 | 8.98 ± 0.06 |
| Compound No. 2 | 6.9 | 8.4 | 8.84 ± 0.07 |
| Compound No. 3 | 6.6 | 8.2 | 8.55 ± 0.25 |
| Compound No. 4 | 6.86 | 8.23 | 8.33 ± 0.15 |
| Compound No. 5 | 6.08 | 7.4 | 7.07 ± 0.11 |
| Compound No. 6 | <5.8 | 7.66 | 7.21 ± 0.20 |
| Compound No. 7 | <5.8 | 7.3 | 6.89 ± 0.29 |
| Compound No. 8 | 6.68 | 7.46 | 7.08 ± 0.18 |
| Compound No. 9 | <6 | 6.69 | — |
| Compound No. 10 | <6 | 6.89 | — |

While the present invention has been described in terms of its specific embodiments, certain modifications and equivalents will be apparent to those skilled in the art and are intended to be included within the scope of the present invention.

We claim:

1. A compound having the structure of Formula I

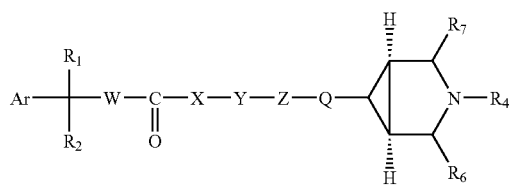

Formula I and its pharmaceutically acceptable salts, pharmaceutically acceptable enantiomers, diastereomers, N-oxides, wherein Ar represents an aryl ring which may be unsubstituted or substituted by one to three substituents independently selected from lower alkyl ($C_1$-$C_4$), lower perhalo alkyl ($C_1$-$C_4$), cyano, hydroxy, nitro, lower alkoxy ($C_1$-$C_4$), lower perhalo alkoxy ($C_1$-$C_4$), unsubstituted amino, N-lower alkyl ($C_1$-$C_4$) amino or N-lower alkyl ($C_1$-$C_4$) amino carbonyl;

$R_1$ represents a hydrogen, hydroxy, hydroxymethyl, amino, alkoxy, carbamoyl or halogen (fluorine, chlorine, bromine or iodine);

$R_2$ represents a $C_3$-$C_7$ cycloalkyl ring in which from 1 to 4 hydrogen atoms are substituted with fluorine atoms, amides or sulphonamide derivatives;

W represents $(CH_2)_p$, where p represents 0 or 1;

X represents no atom;

Y represents $(CH_2)_q$ wherein q represents 0;

Z represents oxygen, sulphur or $NR_{10}$, wherein $R_{10}$ represents hydrogen or $C_{1-6}$ alkyl;

Q represents $(CH_2)_n$ wherein n represents 1 to 4, or $CHR_8$ wherein $R_8$ represents H, OH, $C_{1-6}$ alkyl, alkenyl, alkoxy, or $CH_2CHR_9$ wherein $R_9$ represents H, OH, lower alkyl ($C_1$-$C_4$) or lower alkoxy ($C_1$-$C_4$);

$R_6$ and $R_7$ are independently selected from H, $CH_3$, COOH, $CONH_2$, $NH_2$ or $CH_2NH_2$; and $R_4$ represents a $C_1$-$C_{15}$ saturated or unsaturated aliphatic hydrocarbon group in which from 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on the ring in said arylalkyl, arylalkenyl, hetero arylalkenyl group may be substituted with lower alkyl ($C_1$-$C_4$), lower perhalo alkyl ($C_1$-$C_4$), cyano, hydroxyl, nitro, lower alkoxycarbonyl, halogen, lower alkoxy ($C_1$-$C_4$), lower perhaloalkoxy ($C_1$-$C_4$), unsubstituted amino, N-lower alkylamino ($C_1$-$C_4$) or N-lower alkylamino carbonyl ($C_1$-$C_4$).

2. The compound of claim 1, wherein the compound has the structure of Formula II,

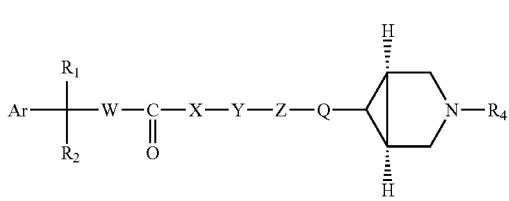

Formula II wherein
Ar represents an aryl which may be unsubstituted or substituted by one to three substituents independently selected from lower alkyl ($C_1$-$C_4$), lower perhalo alkyl ($C_1$-$C_4$), cyano, hydroxy, nitro, lower alkoxy ($C_1$-$C_4$), lower perhalo alkoxy ($C_1$-$C_4$), unsubstituted amino, N-lower alkyl ($C_1$-$C_4$) amino or N-lower alkyl ($C_1$-$C_4$) amino carbonyl;
$R_1$ represents a hydrogen, hydroxy, hydroxymethyl, amino, alkoxy, carbamoyl or halogen (fluorine, chlorine, bromine or iodine);
$R_2$ represents a $C_3$-$C_7$ cycloalkyl ring in which from 1 to 4 hydrogen atoms are substituted with fluorine atoms, amides or sulphonamide derivatives;
W represents $(CH_2)_p$, where p represents 0 or 1;
X represents no atom;
Y represents $(CH_2)_q$ wherein q represents 0;
Z represents oxygen, sulphur or $NR_{10}$, wherein $R_{10}$ represents hydrogen or $C_{1-6}$ alkyl;
Q represents $(CH_2)_n$ wherein n represents 1 to 4, or $CHR_8$ wherein $R_8$ represents H, OH, $C_{1-6}$, alkyl, alkenyl, alkoxy, or $CH_2CHR_9$ wherein $R_9$ represents H, OH, lower alkyl ($C_1$-$C_4$) or lower alkoxy ($C_1$-$C_4$); and
$R_4$ represents a $C_1$-$C_{15}$ saturated or unsaturated aliphatic hydrocarbon group in which from 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on the ring in said arylalkyl, arylalkenyl, hetero arylalkenyl group may be substituted with lower alkyl ($C_1$-$C_4$), lower perhalo alkyl ($C_1$-$C_4$), cyano, hydroxyl, nitro, lower alkoxycarbonyl, halogen, lower alkoxy ($C_1$-$C_4$), lower perhaloalkoxy ($C_1$-$C_4$), unsubstituted amino, N-lower alkylamino ($C_1$-$C_4$) or N-lower alkylamino carbonyl ($C_1$-$C_4$).

3. The compound of claim 1, wherein the compound has the structure of Formula III,

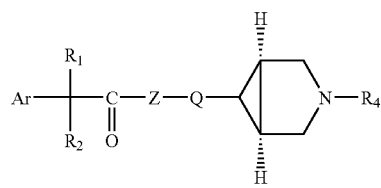

Formula III wherein
Ar represents an aryl which may be unsubstituted or substituted by one to three substituents independently selected from lower alkyl ($C_1$-$C_4$), lower perhalo alkyl ($C_1$-$C_4$), cyano, hydroxy, nitro, lower alkoxy ($C_1$-$C_4$), lower perhalo alkoxy ($C_1$-$C_4$), unsubstituted amino, N-lower alkyl ($C_1$-$C_4$) amino or N-lower alkyl ($C_1$-$C_4$) amino carbonyl;
$R_1$ represents a hydrogen, hydroxy, hydroxymethyl, amino, alkoxy, carbamoyl or halogen (fluorine, chlorine, bromine or iodine);
$R_2$ represents a $C_3$-$C_7$ cycloalkyl ring in which from 1 to 4 hydrogen atoms are substituted with fluorine atoms, amides or sulphonamide derivatives;
Z represents oxygen, sulphur or $NR_{10}$, wherein $R_{10}$ represents hydrogen or $C_{1-6}$ alkyl;
Q represents $(CH_2)_n$ wherein n represents 1 to 4, or $CHR_8$ wherein $R_8$ represents H, OH, $C_{1-6}$, alkyl, alkenyl, alkoxy, or $CH_2CHR_9$ wherein $R_9$ represents H, OH, lower alkyl ($C_1$-$C_4$) or lower alkoxy ($C_1$-$C_4$); and
$R_4$ represents a $C_1$-$C_{15}$ saturated or unsaturated aliphatic hydrocarbon group in which from 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on the ring in said arylalkyl, arylalkenyl, hetero arylalkenyl group may be substituted with lower alkyl ($C_1$-$C_4$), lower perhalo alkyl ($C_1$-$C_4$), cyano, hydroxyl, nitro, lower alkoxycarbonyl, halogen, lower alkoxy ($C_1$-$C_4$), lower perhaloalkoxy ($C_1$-$C_4$), unsubstituted amino, N-lower alkylamino ($C_1$-$C_4$) or N-lower alkylamino carbonyl ($C_1$-$C_4$).

4. The compound of claim 1, wherein the compound has the structure of Formula IV,

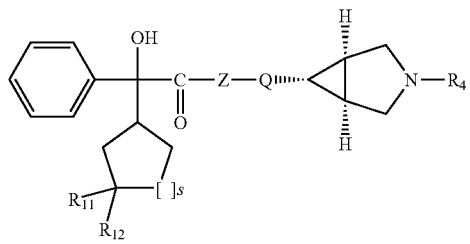

Formula IV wherein $R_{11}$ is hydrogen or fluoro, $R_{12}$ is fluoro, amide or sulphonamide derivatives and s represents 1 to 2;
$R_4$ represents a $C_1$-$C_{15}$ saturated or unsaturated aliphatic hydrocarbon group in which from 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on the ring in said arylalkyl, arylalkenyl, hetero arylalkenyl group may be substituted with lower alkyl ($C_1$-$C_4$), lower perhalo alkyl ($C_1$-$C_4$), cyano, hydroxyl, nitro, lower alkoxycarbonyl, halogen, lower alkoxy ($C_1$-$C_4$), lower perhaloalkoxy ($C_1$-$C_4$), unsubstituted amino, N-lower alkylamino ($C_1$-$C_4$) or N-lower alkylamino carbonyl ($C_1$-$C_4$);

Z represents oxygen, sulphur or $NR_{10}$, wherein $R_{10}$ represents hydrogen or alkyl; and Q represents $(CH_2)_n$ wherein n represents 1 to 4, or $CHR_8$ wherein $R_8$ represents H, OH, $C_{1-6}$, alkyl, alkenyl, alkoxy, or $CH_2CHR_9$ wherein $R_9$ represents H, OH lower alkyl ($C_1$-$C_4$) or lower alkoxy ($C_1$-$C_4$).

5. A compound selected from the group consisting of:

(2R)-(1α,5α,6α)-N-[3-benzyl-3-azabicyclo[3.1.0]hexyl-6-(aminomethyl)-yl]-2-[(1R or 1S)-3,3-difluorocyclopentyl]-2-hydroxy-2-phenylacetamide (Compound No. 1A)

(2R)-(1α,5α,6α)-N-[3-benzyl-3-azabicyclo[3.1.0]hexyl-6-(aminomethyl)-yl]-2-[(1R or 1S)-3,3-difluorocyclopentyl]-2-hydroxy-2-phenylacetamide (Compound No. 1B)

(2R)-(1α,5α,6α)-N-[3-benzyl-3-azabicyclo[3.1.0]hexyl-6-(aminomethyl)-yl]-2-[(1R or 1S, 3R or 3S)-3-fluorocyclopentyl]-2-hydroxy-2-phenylacetamide (Compound No. 2)

(2R or 2S)-(1α,5α,6α)-N-[3-benzyl-3-azabicyclo[3.1.0]hexyl-6-(aminomethyl)-yl ]-2-[(1R or 1S)-3,3-difluorocyclopentyl]-2-hydroxy-2-phenylacetamide (Compound No. 3)

(2R or 2S)-(1α,5α,6α)-N-[3-benzyl-3-azabicyclo[3.1.0]hexyl-6-(aminomethyl)-yl ]-2-[(1R or 1S, 3R or 3S)-3-fluorocyclopentyl]-2-hydroxy-2-phenylacetamide (Compound No. 4)

(2R)-(1α,5α,6α)-N-[3-benzyl-3-azabicyclo[3.1.0]hexyl-6-(aminomethyl)-yl]-2-[(1R or 1S, 3R or 3S)-3-phenylacetylamino cyclopentyl]-2-hydroxy-2-phenylacetamide (Compound No. 5)

(2R)-(1α,5α,6α)-N-[3-benzyl-3-azabicyclo[3.1.0]hexyl-6-(aminomethyl)-yl]-2-[(1R or 1S, 3R or 3S)-3-(4-nitrophenyl) sulphonylaminocyclopentyl]-2-hydroxy-2-phenylacetamide (Compound No. 6)

(2R)-(1α,5α,6α)-N-[3-benzyl-3-azabicyclo[3.1.0]hexyl-6-(aminomethyl)-yl]-2-[(1R or 1S, 3R or 3S)-3-phenylsulphonylamino cyclopentyl]-2-hydroxy-2-phenylacetamide (Compound No. 7)

(2R)-(1α,5α,6α)-N-[3-benzyl-3-azabicyclo[3.1.0]hexyl-6-(aminomethyl)-yl]-2-[(1R or 1S, 3R or 3S)-3-benzyloxyacetylaminocyclopentyl]-2-hydroxy-2-phenylacetamide (Compound No. 8)

(2R)-(1α,5α,6α)-N-[3-benzyl-3-azabicyclo[3.1.0]hexyl-6-(aminomethyl)-yl]-2-[(1R or 1S, 3R or 3S)-3-(4-methoxyphenyl) sulphonylaminocyclo pentyl]-2-hydroxy-2-phenylacetamide (Compound No. 9); and (2R)-(1α,5α,6α)-N-[3-benzyl-3-azabicyclo[3.1.0]hexyl-6-(aminomethyl)-yl]-2-[(1R or 1S, 3R or 3S)-3-(4-bromophenyl)sulphonylamino cyclopentyl]-2-hydroxy-2-phenylacetamide (Compound No. 10).

6. A pharmaceutical composition comprising a therapeutically effective amount of a compound of claim 1 together with pharmaceutically acceptable carriers, excipients or diluents.

7. A method for treatment of an animal or human suffering from a disease or disorder of the respiratory, urinary and gastrointestinal systems, wherein the disease or disorder is mediated through muscarinic receptors, and wherein the disease or disorder is urinary incontinence, lower urinary tract symptoms (LUTS), bronchial asthma, chronic obstructive pulmonary disorders (COPD), pulmonary fibrosis, irritable bowel syndrome, obesity, diabetes and gastrointestinal hyperkinesis, the method comprising administering to said animal or human, a therapeutically effective amount of a compound having the structure of Formula I

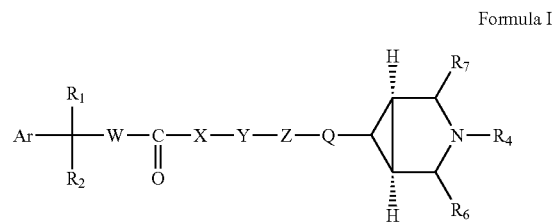

Formula I and its pharmaceutically acceptable salts, pharmaceutically acceptable enantiomers, diastereomers, N-oxides, wherein Ar represents an aryl which may be unsubstituted or substituted by one to three substituents independently selected from lower alkyl ($C_1$-$C_4$), lower perhalo alkyl ($C_1$-$C_4$), cyano, hydroxy, nitro, lower alkoxy ($C_1$-$C_4$), lower perhalo alkoxy ($C_1$-$C_4$), unsubstituted amino, N-lower alkyl ($C_1$-$C_4$) amino or N-lower alkyl ($C_1$-$C_4$) amino carbonyl;

$R_1$ represents a hydrogen, hydroxyhydroxymethyl, amino, alkoxy, carbamoyl or halogen (fluorine, chlorine, bromine and iodine);

$R_2$ represents a $C_3$-$C_7$ cycloalkyl ring in which from 1 to 4 hydrogen atoms are substituted with fluorine atoms, amides or sulphonamide derivatives;

W represents $(CH_2)_p$, where p represents 0 to 1;

X represents no atom;

Y represents $(CH_2)_q$ wherein q represents 0;

Z represents oxygen, sulphur, $NR_{10}$, wherein $R_{10}$ represents hydrogen or $C_{16}$ alkyl;

Q represents $(CH_2)_n$ wherein n represents 1 to 4, or $CHR_8$ wherein $R_8$ represents H, OH, $C_{1-6}$, alkyl, alkenyl, alkoxy, or $CH_2CHR_9$ wherein $R_9$ represents H, OH, lower alkyl ($C_1$-$C_4$) or lower alkoxy ($C_1$-$C_4$);

$R_6$ and $R_7$ are independently selected from H, $CH_3$, COOH, $CONH_2$, $NH_2$ or $CH_2NH_2$; and $R_4$ represents a $C_1$-$C_{15}$ saturated or unsaturated aliphatic hydrocarbon group in which from 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on the ring in said arylalkyl, arylalkenyl, hetero arylalkenyl group may be substituted with lower alkyl ($C_1$-$C_4$), lower perhalo alkyl ($C_1$-$C_4$), cyano, hydroxyl, nitro, lower alkoxycarbonyl, halogen, lower alkoxy ($C_1$-$C_4$), lower perhaloalkoxy ($C_1$-$C_4$), unsubstituted amino, N-lower alkylamino ($C_1$-$C_4$) or N-lower alkylamino carbonyl ($C_1$-$C_4$).

8. The method of claim 7, wherein the compound has the structure of Formula II, Formula II

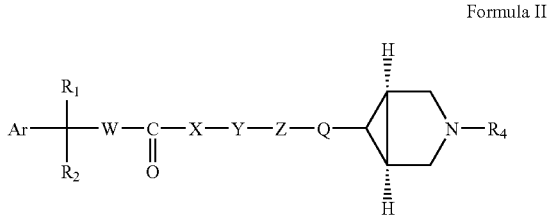

wherein
- Ar represents an aryl which may be unsubstituted or substituted by one to three substituents independently selected from lower alkyl ($C_1$-$C_4$), lower perhalo alkyl ($C_1$-$C_4$), cyano, hydroxy, nitro, lower alkoxy ($C_1$-$C_4$), lower perhalo alkoxy ($C_1$-$C_4$), unsubstituted amino, N-lower alkyl ($C_1$-$C_4$) amino or N-lower alkyl ($C_1$-$C_4$) amino carbonyl;
- $R_1$ represents a hydrogen, hydroxy, hydroxymethyl, amino, alkoxy, carbamoyl or halogen (fluorine, chlorine, bromine or iodine);
- $R_2$ represents a $C_3$-$C_7$ cycloalkyl ring in which from 1 to 4 hydrogen atoms are substituted with fluorine atoms, amides or sulphonamide derivatives;
- W represents $(CH_2)_p$, where p represents 0 or 1;
- X represents no atom;
- Y represents $(CH_2)_q$ wherein q represents 0;
- Z represents oxygen, sulphur or $NR_{10}$, wherein $R_{10}$ represents hydrogen or alkyl;
- Q represents $(CH_2)_n$ wherein n represents 1 to 4, or $CHR_8$ wherein $R_8$ represents H, OH, $C_{1-6}$, alkyl, alkenyl, alkoxy, or $CH_2CHR_9$ wherein $R_9$ represents H, OH, lower alkyl ($C_1$-$C_4$) or lower alkoxy ($C_1$-$C_4$; and
- $R_4$ represents a $C_1$-$C_{15}$ saturated or unsaturated aliphatic hydrocarbon group in which from 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on the ring in said arylalkyl, arylalkenyl, hetero arylalkenyl group may be substituted with lower alkyl ($C_1$-$C_4$), lower perhalo alkyl ($C_1$-$C_4$), cyano, hydroxyl, nitro, lower alkoxycarbonyl, halogen, lower alkoxy ($C_1$-$C_4$), lower perhaloalkoxy ($C_1$-$C_4$), unsubstituted amino, N-lower alkylamino ($C_1$-$C_4$) or N-lower alkylamino carbonyl ($C_1$-$C_4$).

9. The method of claim 7, wherein the compound has the structure of Formula III, Formula III

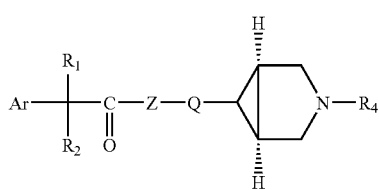

wherein
- Ar represents an aryl which may be unsubstituted or substituted by one to three substituents independently selected from lower alkyl ($C_1$-$C_4$), lower perhalo alkyl ($C_1$-$C_4$), cyano, hydroxy, nitro, lower alkoxy ($C_1$-$C_4$), lower perhalo alkoxy ($C_1$-$C_4$), unsubstituted amino, N-lower alkyl ($C_1$-$C_4$) amino or N-lower alkyl ($C_1$-$C_4$) amino carbonyl;
- $R_1$ represents a hydrogen, hydroxy, hydroxymethyl, amino, alkoxy, carbamoyl or halogen (fluorine, chlorine, bromine or iodine);
- $R_2$ represents a $C_3$-$C_7$ cycloalkyl ring in which from 1 to 4 hydrogen atoms are substituted with fluorine atoms, amides or sulphonamide derivatives;
- Z represents oxygen, sulphur or $NR_{10}$, wherein $R_{10}$ represents hydrogen or $C_{1-6}$ alkyl;
- Q represents $(CH_2)_n$ wherein n represents 1 to 4, or $CHR_8$ wherein $R_8$ represents H, OH, $C_{1-6}$, alkyl, alkenyl, alkoxy, or $CH_2CHR_9$ wherein $R_9$ represents H, OH, lower alkyl ($C_1$-$C_4$) or lower alkoxy ($C_1$-$C_4$); and
- $R_4$ represents a $C_1$-$C_{15}$ saturated or unsaturated aliphatic hydrocarbon group in which from 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on the ring in said arylalkyl, arylalkenyl, hetero arylalkenyl group may be substituted with lower alkyl ($C_1$-$C_4$), lower perhalo alkyl ($C_1$-$C_4$), cyano, hydroxyl, nitro, lower alkoxycarbonyl, halogen, lower alkoxy ($C_1$-$C_4$), lower perhaloalkoxy ($C_1$-$C_4$), unsubstituted amino, N-lower alkylamino ($C_1$-$C_4$) or N-lower alkylamino carbonyl 1-$C_4$).

10. The method of claim 7, wherein the compound has the structure of Formula IV, Formula IV

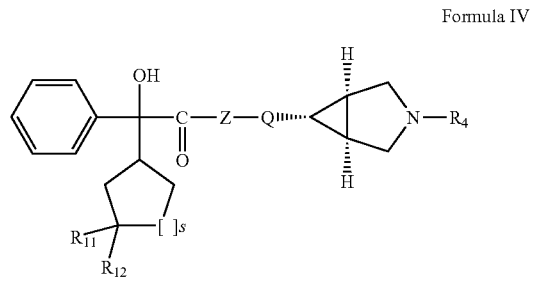

wherein
- $R_{11}$ is hydrogen or fluoro, $R_{12}$ is fluoro, amide or sulphonamide derivatives and s represents 1 to 2;
- $R_4$ represents a $C_1$-$C_{15}$ saturated or unsaturated aliphatic hydrocarbon group in which from 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on the ring in said arylalkyl, arylalkenyl, hetero arylalkenyl group may be substituted with lower alkyl ($C_1$-$C_4$), lower perhalo alkyl ($C_1$-$C_4$), cyano, hydroxyl, nitro, lower alkoxycarbonyl, halogen, lower alkoxy ($C_1$-$C_4$), lower perhaloalkoxy ($C_1$-$C_4$), unsubstituted amino, N-lower alkylamino ($C_1$-$C_4$) or N-lower alkylamino carbonyl ($C_1$-$C_4$);
- Z represents oxygen, sulphur or $NR_{10}$, wherein $R_{10}$ represents hydrogen or $C_{1-6}$ alkyl; and Q represents $(CH_2)_n$ wherein n represents 1 to 4, or $CHR_8$ wherein $R_8$ represents H, OH, $C_{1-6}$, alkyl, alkenyl, alkoxy, or $CH_2CHR_9$ wherein $R_9$ represents H, OH, lower alkyl $(C_1-C_4)$ or lower alkoxy $(C_1-C_4)$.

11. The method for treatment of an animal or human suffering from a disease or disorder of the respiratory, urinary and gastrointestinal systems, wherein the disease or disorder is mediated through the muscarinic receptors, and wherein the disease or disorder is urinary incontinence, lower urinary tract symptoms (LUTS), bronchial asthma, chronic obstructive pulmonary disorders (COPD), pulmonary fibrosis, irritable bowel syndrome, obesity, diabetes and gastrointestinal hyperkinesis, the method comprising administering to said animal or human a therapeutically effective amount of a pharmaceutical composition of claim 6.

12. A process of preparing a compound of Formula I

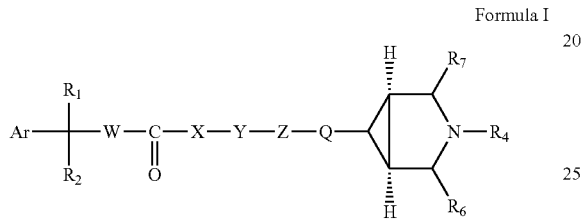

Formula I and its pharmaceutically acceptable salts, pharmaceutically acceptable enantiomers, diastereomers, N-oxides, wherein
Ar represents an aryl which may be unsubstituted or substituted by one to three substituents independently selected from lower alkyl $(C_1-C_4)$, lower perhalo alkyl $(C_1-C_4)$, cyano, hydroxy, nitro, lower alkoxy $(C_1-C_4)$, lower perhalo alkoxy $(C_1-C_4)$, unsubstituted amino, N-lower alkyl $(C_1-C_4)$ amino or N-lower alkyl $(C_1-C_4)$ amino carbonyl;

$R_1$ represents a hydrogen, hydroxy, hydroxymethyl, amino, alkoxy, carbamoyl or halogen (fluorine, chlorine, bromine and iodine);

$R_2$ represents a $C_3-C_7$ cycloalkyl ring in which from 1 to 4 hydrogen atoms are substituted with fluorine atoms, amides or sulphonamide derivatives;

W represents $(CH_2)_p$, where p represents 0 to 1;
X represents no atom;
Y represents $(CH_2)_q$ wherein q represents 0;
Z represents oxygen, sulphur, $NR_{10}$, wherein $R_{10}$ represents hydrogen or $C_{1-6}$ alkyl;
Q represents $(CH_2)_n$ wherein n represents 1 to 4, or $CHR_8$ wherein $R_8$ represents H, OH, $C_{1-6}$, alkyl, alkenyl, alkoxy, or $CH_2CHR_9$ wherein $R_9$ represents H, OH, lower alkyl $(C_1-C_4)$ or lower alkoxy $(C_1-C_4)$;
$R_6$ and $R_7$ are independently selected from H, $CH_3$, COOH, $CONH_2$, $NH_2$ or $CH_2NH_2$; and
$R_4$ represents a $C_1-C_{15}$ saturated or unsaturated aliphatic hydrocarbon group in which from 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on the ring in said arylalkyl, arylalkenyl, hetero arylalkenyl group may be substituted with lower alkyl $(C_1-C_4)$, lower perhalo alkyl $(C_1-C_4)$, cyano, hydroxyl, nitro, lower alkoxycarbonyl, halogen, lower alkoxy $(C_1-C_4)$, lower perhaloalkoxy $(C_1-C_4)$, unsubstituted amino, N-lower alkylamino $(C_1-C_4)$ or N-lower alkylamino carbonyl $(C_1-C_4)$, comprising (a) condensing a compound of Formula VI with a compound of Formula V

FORMULA VI

FORMULA V wherein Ar, $R_1$, $R_2$, W, X, Y, Z, Q, $R_6$ and $R_7$ have the same meanings as defined earlier for Formula I, to give a protected compound of Formula VII wherein Ar, $R_1$, $R_2$, W, X, Y, Z, Q, $R_6$ and $R_7$ are the same as defined earlier and P is a protecting group for an amino group,

FORMULA VII (b) deprotecting the compound of Formula VII in the presence of a deprotecting agent to give an unprotected intermediate of Formula VIII wherein Ar, $R_1$, $R_2$, W, X, Y, Z, Q, $R_6$ and $R_7$ are the same as defined earlier, and

FORMULA VIII (c) N-alkylating or benzylating the intermediate of Formula VIII with a suitable alkylating agent or benzylating agent to give a compound of Formula I.

13. The process according to claim 12 wherein P is any protecting group for an amino group and is selected from the group consisting of benzyl or t-butyloxy carbonyl groups.

14. The process according to claim 12 wherein the reaction of a compound of Formula V with a compound of Formula VI to give a compound of Formula VII is carried out in the presence of a condensing agent which is selected from the group consisting of 1-(3-dimethylaminopropyl)-3-ethyl carbodiimide hydrochloride (EDC) and 1,8-diazabicyclo[5.4.0]undec-7-ene (DBU).

15. The process according to claim 12 wherein the reaction of a compound of Formula V with a compound of Formula VI is carried out at about 0-140° C.

16. The process according to claim 12 wherein the deprotection of a compound of Formula VII to give a compound of Formula VIII is carried out with a deprotecting agent which is selected from the group consisting of palladium on carbon, trifluoroacetic acid (TFA) and hydrochloric acid.

17. The process according to claim 12 wherein the N-alkylation or benzylation of a compound of Formula VIII to give a compound of Formula I is carried out with a suitable alkylating or benzylating agent, L-$R_4$, wherein L is any leaving group and $R_4$ is the same as defined earlier.

18. The process according to claim 17 wherein the leaving group is selected from the group consisting of halogen, O-mestyl and O-tosyl group.

19. A process for preparing a compound of Formula IV

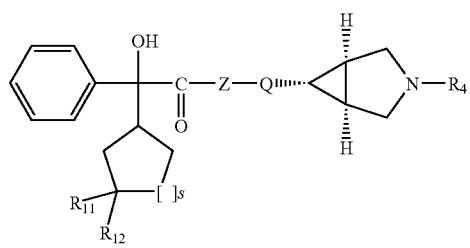

Formula IV and its pharmaceutically acceptable salts, pharmaceutically acceptable enantiomers, diastereomers, N-oxides, wherein $R_{11}$ is hydrogen or fluoro, $R_{12}$ is fluoro, amide or sulphonamide derivatives and s represents 1 to 2;

Z represents oxygen, sulphur, $NR_{10}$, wherein $R_{10}$ represents hydrogen, $C_{1-6}$ alkyl;

Q represents $(CH_2)_n$ wherein n represents 1 to 4, or $CHR_8$ wherein $R_8$ represents H, OH, $C_{1-6}$, alkyl, alkenyl, alkoxy, or $CH_2CHR_9$ wherein $R_9$ represents H, OH, lower alkyl ($C_1$-$C_4$) or lower alkoxy ($C_1$-$C_4$); and $R_4$ represents a $C_1$-$C_{15}$ saturated or unsaturated aliphatic hydrocarbon group in which from 1 to 6 hydrogen atoms may be substituted with the group independently selected from halogen, arylalkyl, arylalkenyl, heteroarylalkyl or heteroarylalkenyl having 1 to 2 hetero atoms selected from a group consisting of nitrogen, oxygen and sulphur atoms with an option that any 1 to 3 hydrogen atoms on the ring in said arylalkyl, arylalkenyl, hetero arylalkenyl group may be substituted with lower alkyl ($C_1$-$C_4$), lower perhalo alkyl ($C_1$-$C_4$), cyano, hydroxyl, nitro, lower alkoxycarbonyl, halogen, lower alkoxy ($C_1$-$C_4$), lower perhaloalkoxy ($C_1$-$C_4$), unsubstituted amino, N-lower alkylamino ($C_1$-$C_4$), N-lower alkylamino carbonyl ($C_1$-$C_4$), comprising:

(i) condensing a compound of Formula IX with a compound of Formula X

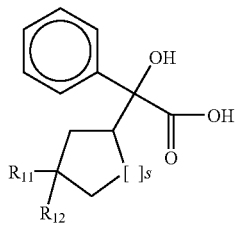

FORMULA IX

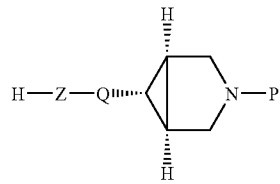

FORMULA X where Z, Q, $R_{11}$, $R_{12}$ and s have the same meanings as defined earlier for Formula IV, to give a protected compound of Formula XI,

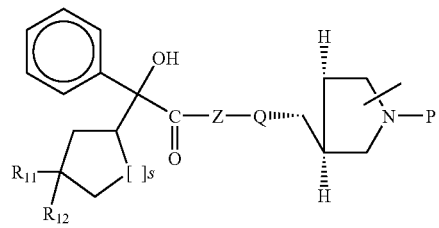

FORMULA XI (ii) deprotecting the compound of Formula XI in the presence of a deprotecting agent to give an unprotected intermediate of Formula XII where Z, Q, $R_{11}$, $R_{12}$, s have the same meanings as defined earlier, and

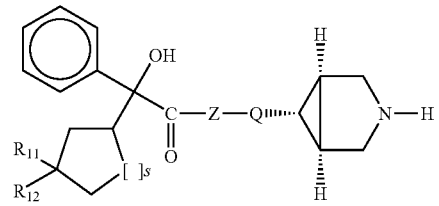

FORMULA XII (iii) the intermediate of Formula XII is N-alkylated or benzylated with a suitable alkylating or benzylating agent to give a compound of Formula IV wherein Z, Q, $R_{11}$, $R_{12}$, and s are the same as defined earlier; or (b) (i) condensing a compound of Formula IX with a compound of Formula XIII

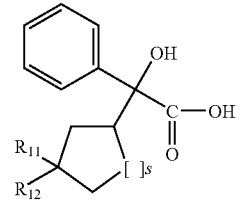

FORMULA IX

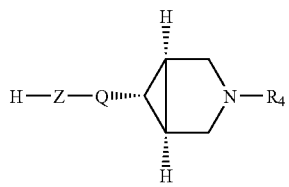

FORMULA XIII where Z, Q, R$_4$ and s have the same meanings as defined earlier for Formula IV; or (c) (i) condensing a compound of Formula XIV with a compound of Formula X

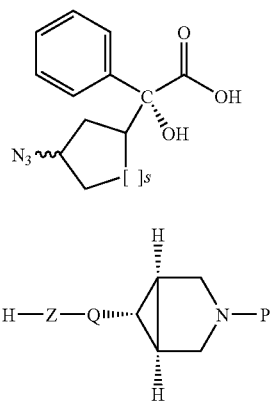

FORMULA XIV

FORMULA X

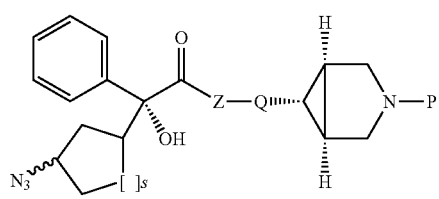

where Z, Q and s have the same meanings as defined earlier for Formula IV, to give a protected compound of Formula XV, Formula XV

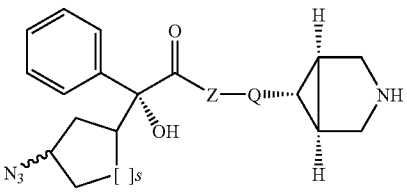

(ii) deprotecting the compound of Formula XV in the presence of a deprotecting agent to give an unprotected intermediate of Formula XVI, wherein Z, Q and s have the same meanings as defined earlier, Formula XVI (iii) N-alkylating or benzylating the intermediate of Formula XVI with a suitable alkylating or benzylating agent to give a compound of Formula XVI, wherein Z, Q, R$_4$ and s are the same as defined earlier, Formula XVII

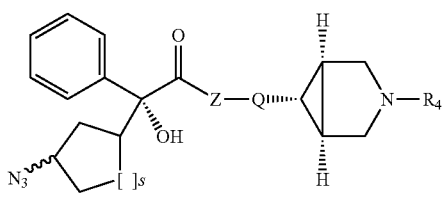

(iv) reducing the compound of Formula XVII to give a compound of Formula XVII, wherein Z, Q, R$_4$ and s have the same meanings as defined earlier, and Formula XVIII

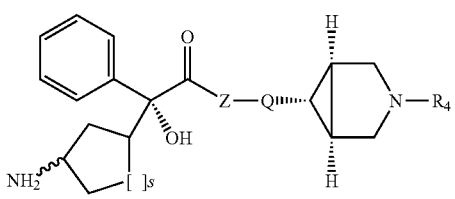

(v) reacting a compound of Formula XVIII with acid chlorides to give a compound of Formula IV (R$_{11}$=H, R$_{12}$=substituted sulfonamide).

20. The process according to claim 19 wherein P is a protecting group for an amino group and is selected from the group consisting of benzyl or t-butoxy carbonyl groups.

21. The process according to claim 19 wherein the reaction of a compound of Formula IX with a compound of Formula X to give a compound of Formula XI, the reaction of a compound of Formula XIII with a compound of Formula IX or the reaction of a compound of Formula XIV with a compound of Formula X is carried out in the presence of a condensing agent which is selected from the group consisting of 1-(3-dimethyl aminopropyl)-3-ethyl-carbodiimide hydrochloride (EDC) and 1,8-diazabicyclo[5.4.0]undec-7-ene (DBU).

22. The process according to claim 19 wherein the reaction of a compound of Formula IX with a compound of Formula X, the reaction of a compound of Formula XIII with a compound of Formula IX or the reaction of a compound of Formula XIV with a compound of Formula X is carried out at about 0-14° C.

23. The process according to claim 19 wherein the deprotection of a compound of Formula XI to give a compound of Formula XII or the deprotection of a compound of Formula V to give a compound of Formula XVI is carried out with a deprotecting agent which is selected from the group consisting of palladium on carbon, trifluoroacetic acid (TFA) and hydrochloric acid.

24. The process according to claim 19 wherein the N-alkylation or benzylation of a compound of Formula XII to give a compound of Formula IV or the N-alkylation or benzylation of a compound of Formula XVI to give a compound of Formula XVII is carried out with a suitable alkylating or benzylating agent, L-$R_4$, wherein L is any leaving group and $R_4$ is the same as defined earlier.

25. The process according to claim 24 wherein the leaving group is selected from the group consisting of halogen, O-mestyl and O-tosyl group.

26. The process according to claim 19 wherein the reduction of a compound of Formula XVII to give a compound of Formula XVIII is carried out with triphenylphosphine.

27. The process according to claim 19 wherein the acid chlorides used in the reaction of a compound of Formula XVIII with acid chlorides is selected from the group consisting of phenylacetyl chloride, 4-nitrophenylsulfonyl chloride, benzene sulfonyl chloride, benzyloxyacetyl chloride, 4-methoxyphenylsulfonyl chloride and 4-bromophenylsulfonyl chloride.

* * * * *

UNITED STATES PATENT AND TRADEMARK OFFICE
CERTIFICATE OF CORRECTION

| | |
|---|---|
| PATENT NO. | : 7,288,562 B2 |
| APPLICATION NO. | : 10/525439 |
| DATED | : October 30, 2007 |
| INVENTOR(S) | : Mehta et al. |

It is certified that error appears in the above-identified patent and that said Letters Patent is hereby corrected as shown below:

Front page, Attorney section - "Jaydeip" should read --Jayadeep--
Front page, Abstract - "hexane's" should read --hexanes--
Front page, Abstract - "MUSCARINIC" should read --muscarinic--
Front page, Abstract - "inter-ail" should read --inter-aila--
Front page, Abstract - "MUSCARINIC" should read --muscarinic--
Front page, Abstract - "The invention" is the start of the second paragraph, which should be indented
Column 2, Line 65 - "in vivo" should read --*in vivo*--
Column 5, Line 46 - "in vivo" should read --*in vivo*--
Column 5, Line 47 - "in vivo" should read --*in vivo*--
Column 9, Line 51 - "Formula XIII" should read --Formula XII--
Column 15, Line 63 - "NH-CO-NH" should read --NH-CO-    NH--
Column 16, Lines 49-55 belongs in Column 15 under Line 33, above table
Column 17, Line 7 - "in vivo" should read --*in vivo*--
Column 17, Line 39 - "-N-3-" should read -- -N-[3- --
Column 20, Line 13 - "3S-3-" should read --3S]-3- --
Column 20, Line 19 - "(m, 9)" should read --(m, 9H)--
Column 21, Line 2 - "(aminomethyly)" should read --(aminomethyl)--
Column 21, Line 26 - "3)-3-" should read --3S)-3- --
Column 22, Line 6 - "5.304.99" should read --5.30-4.99--
Column 22, Line 40 - "water" should read --water.--
Column 23, Line 17 - "(m,1)" should read --(m,1H)--
Column 23, Line 40 - "3S)3-phenylacetylamino" should read
--3S)-3-phenylacetylamino--
Column 23, Line 40 - "cydopentyl" should read --cyclopentyl--
Column 23, Line 57 - "-34(4-" should read -- -3-(4- --
Column 24, Line 19 - "]-2[" should read --]-2-[--
Column 29, Line 14 - "hydrogen or alkyl" should read --hydrogen or C1-6 alkyl--
Column 4, Line 4 - "hetero arylalkenyl" should read --heteroarylalkenyl--
Column 7, Line 64 - "acetonitriie" should read --acetonitrile--
Column 8, Line 15 - "(CH2)p where q=0" should read --(CH2)q, where q=0--

UNITED STATES PATENT AND TRADEMARK OFFICE
CERTIFICATE OF CORRECTION

PATENT NO. : 7,288,562 B2
APPLICATION NO. : 10/525439
DATED : October 30, 2007
INVENTOR(S) : Mehta et al.

It is certified that error appears in the above-identified patent and that said Letters Patent is hereby corrected as shown below:

Column 20, Line 62 - "step-d-d" should read --step-d--
Column 24, Line 34 - "(1 , , 6)" should read --(1, 5, 6)*--

Signed and Sealed this

Nineteenth Day of August, 2008

JON W. DUDAS
*Director of the United States Patent and Trademark Office*